US008673302B2

(12) United States Patent
Goetsch et al.

(10) Patent No.: US 8,673,302 B2
(45) Date of Patent: Mar. 18, 2014

(54) ANTI-CMET ANTIBODY AND ITS USE FOR THE DETECTION AND THE DIAGNOSIS OF CANCER

(75) Inventors: Liliane Goetsch, Ayze (FR); Alexandra Jouhanneaud, Bonneville (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 13/391,435

(22) PCT Filed: Aug. 23, 2010

(86) PCT No.: PCT/EP2010/062271
§ 371 (c)(1),
(2), (4) Date: Feb. 21, 2012

(87) PCT Pub. No.: WO2011/020925
PCT Pub. Date: Feb. 24, 2011

(65) Prior Publication Data
US 2012/0149031 A1   Jun. 14, 2012

Related U.S. Application Data

(60) Provisional application No. 61/235,864, filed on Aug. 21, 2009, provisional application No. 61/348,005, filed on May 25, 2010.

(30) Foreign Application Priority Data

Aug. 21, 2009   (EP) .................................... 09305777

(51) Int. Cl.
*A61K 38/00* (2006.01)
(52) U.S. Cl.
USPC ...... 424/133.1; 424/143.1; 435/7.4; 435/326; 530/389.1
(58) Field of Classification Search
None
See application file for complete search history.

(56) References Cited

U.S. PATENT DOCUMENTS

2011/0097262 A1* 4/2011 Goetsch et al. .............. 424/1.49

FOREIGN PATENT DOCUMENTS

| EP | 2 014 681 A1 | 1/2009 |
| WO | WO2007/090807 A1 | 8/2007 |
| WO | WO2009/029591 A2 | 3/2009 |

OTHER PUBLICATIONS

Rudikoff et al (PNAS, 1982, 79:1979).*
MacCallum et al (J of Mol Biol, 1996, 262:732-745).*
De Pascalis et al (J of Immunol, 2002, 169:3076-3084).*
Casset et al (Biochem and Biophys Res Commun, 2003, 307:198-205).*
Vajdos et al (J Mol Biol, 2002, 320:415-428).*
Holm et al (Mol Immunol, 2007:1075-1084).*
Chen et al (J Mol Biol, 1999, 293:865-881).*
Wu et al (J Mol Biol, 1999, 294:151-162).*
Knudsen et al (Appl Immunohistochem Mol Morphol, 2009, 17:57-67, labeled as pp. 1-26 on the article provided).*
Corvaia, N. et al., "First Bivalent Fully Antagonist Anti-c-Met Antibody Targeting the c-Met Receptor: I) In Vitro Mechanism of Action," 2009 AACR Annual Meeting (2009).
Knudsen, B. S. et al., "A Novel Multipurpose Monoclonal Antibody for Evaluating Human c-Met Expression in Preclinical and Clinical Settings," *Appl. Immunohist. Mol. Morphol.*, 17:57-67 (2009).
Winkler, K. et al., "Changing the Antigen Binding Specificity by Single Point Mutation sof an Anti-p24 (HIV-1) Antibody," *J Immunol.*, 165:4505-4514 (2000).
International Search Report PCT/EP2010/062271 dated Nov. 29, 2010.

* cited by examiner

*Primary Examiner* — Misook Yu
*Assistant Examiner* — Julie Wu
(74) *Attorney, Agent, or Firm* — Finnegan, Henderson, Farabow, Garrett & Dunner, LLP

(57) ABSTRACT

The present invention relates to the field of prognosis and/or diagnosis of a proliferative disease in a patient. More particularly, the invention relates to antibodies capable of binding to the human cMet receptor, as well as the amino acid and nucleic acid sequences coding for these antibodies. The invention likewise comprises the use of said antibodies, and corresponding processes, for detecting and diagnosing pathological hyperproliferative oncogenic disorders associated with expression of cMet. In certain embodiments, the disorders are oncogenic disorders associated with increased expression of cMet polypeptide relative to normal or any other pathology connected with the overexpression of cMet. The invention finally comprises products and/or compositions or kits comprising at least such antibodies for the prognosis or diagnostic of certain cancers.

23 Claims, 9 Drawing Sheets

A) Breastcancer

3+    2+    1+    neg

B) Stomach cancer

3+    2+    1+    neg

ANTI-CMET ANTIBODY AND ITS USE FOR THE DETECTION AND THE DIAGNOSIS OF CANCER

CROSS REFERENCE TO RELATED APPLICATIONS

Figure 1A:
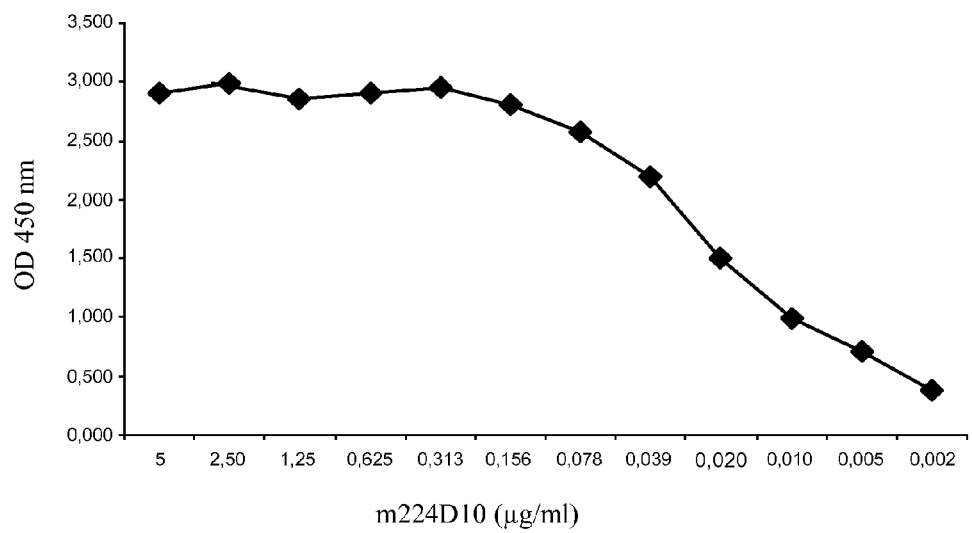

This is a national stage application under 35 U.S.C. §371 of International Application No. PCT/EP2010/062271, filed Aug. 23, 2010, which claims the benefit under 35 U.S.C. §119(e) of U.S. provisional patent applications Nos. 61/235,864, filed Aug. 21, 2009, and 61/348,005, filed May 25, 2010, and the benefit under 35 U.S.C. §365(b) of European Patent Application No. 09305777.6, filed Aug. 21, 2009.

REFERENCE TO SEQUENCE LISTING SUBMITTED ELECTRONICALLY

An official copy of the sequence listing is submitted electronically via EFS-Web as an ASCII formatted sequence listing with a file named "SequenceListing.txt", created on Feb. 20, 2012, and having a size of 16 kilobytes. The sequence listing contained in this ASCII formatted document is part of the specification and is herein incorporated by reference in its entirety.

The present invention relates to the field of prognosis and/or diagnosis of a proliferative disease in a patient. More particularly, the invention relates to a novel antibody capable of binding specifically to the human cMet receptor, as well as the amino acid and nucleic acid sequences coding for this antibody. The invention likewise comprises the use of said antibody, and corresponding processes, for detecting and diagnosing pathological hyperproliterative oncogenic disorders associated with expression of cMet. In certain embodiments, the disorders are oncogenic disorders associated with increased expression of cMet polypeptide relative to normal or any other pathology connected with the overexpression of cMet. The invention finally comprises products and/or compositions or kits comprising at least such antibody for the prognosis or diagnostic of certain cancers.

Receptor tyrosine kinase (RTK) targeted agents such as trastuzumab, cetuximab, bevacizumab, imatinib and gefitinib inhibitors have illustrated the interest of targeting this protein class for treatment of selected cancers.

cMet, is the prototypic member of a sub-family of RTKs which also includes RON and SEA. The cMet RTK family is structurally different from other RTK families and is the only known high-affinity receptor for hepatocyte growth factor (HGF), also called scatter factor (SF) [D. P. Bottaro et al., Science 1991, 251: 802-804; L. Naldini et al., Eur. Mol. Biol. Org. J. 1991, 10:2867-2878]. cMet and HGF are widely expressed in a variety of tissue and their expression is normally restricted to cells of epithelial and mesenchymal origin respectively [M. F. Di Renzo et al., Oncogene 1991, 6:1997-2003; E. Sonnenberg et al., J. Cell. Biol. 1993, 123:223-235]. They are both required for normal mammalian development and have been shown to be particularly important in cell migration, morphogenic differentiation, and organization of the three-dimensional tubular structures as well as growth and angiogenesis [F. Baldt et al., Nature 1995, 376:768-771; C. Schmidt et al., Nature. 1995:373:699-702; Tsarfaty et al., Science 1994, 263:98-101]. While the controlled regulation of cMet and HGF have been shown to be important in mammalian development, tissue maintenance and repair [Nagayama T, Nagayama M, Kohara S, Kamiguchi H, Shibuya M, Katoh Y, Itoh J, Shinohara Y., Brain Res. 2004, 5; 999(2): 155-66; Tahara Y, Ido A, Yamamoto S, Miyata Y, Uto H, Hori T, Hayashi K, Tsubouchi H., J Pharmacol Exp Ther. 2003, 307(1):146-51], their dysregulation is implicated in the progression of cancers.

Aberrant signalling driven by inappropriate activation of cMet is one of the most frequent alteration observed in human cancers and plays a crucial role in tumorigenesis and metastasis [Birchmeier et al., Nat. Rev. Mol. Cell. Biol. 2003, 4:915-925; L. Trusolino and Comoglio P. M., Nat. Rev. Cancer. 2002, 2(4):289-300].

Inappropriate cMet activation can arise by ligand-dependent and independent mechanisms, which include overexpression of cMet, and/or paracrine or autocrine activation, or through gain in function mutation [J. G. Christensen, Burrows J. and Salgia R., Cancer Letters. 2005, 226:1-26]. However an oligomerization of cMet receptor, in presence or in absence of the ligand, is required to regulate the binding affinity and binding kinetics of the kinase toward ATP and tyrosine-containing peptide substrates [Hays J L, Watowich S J, Biochemistry, 2004 Aug. 17, 43:10570-8]. Activated cMet recruits signalling effectors to its multidocking site located in the cytoplasm domain, resulting in the activation of several key signalling pathways, including Ras-MAPK, PI3K, Src and Stat3 [Gao C F, Vande Woude G F, Cell Res. 2005, 15(1):49-51; Furge K A, Zhang Y W, Vande Woude G F, Oncogene. 2000, 19(49):5582-9]. These pathways are essential for tumour cell proliferation, invasion and angiogenesis and for evading apoptosis [Furge K A, Zhang Y W, Vande Woude G F, Oncogene, 2000, 19(49):5582-9; Gu H, Neel B G, Trends Cell Biol. 2003 Mar. 13(3):122-30; Fan S, Ma Y X, Wang J A, Yuan R Q, Meng Q, Cao Y, Laterra J J, Goldberg I D, Rosen E M, Oncogene. 2000 Apr. 27, 19(18):2212-23]. In addition, a unique facet of the cMet signalling relative to other RTK is its reported interaction with focal adhesion complexes and non kinase binding partners such as α6β4 integrins [Trusolino L, Bertotti A, Comoglio P M, Cell. 2001, 107:643-54], CD44v6 [Van der Voort R, Taher T E, Wielenga V J, Spaargaren M, Prevo R, Smit L, David G, Hartmann G, Gherardi E, Pals S T, J Biol. Chem. 1999, 274(10):6499-506], Plexin B1 or semaphorins [Giordano S, Corso S, Conrotto P, Artigiani S, Gilestro G, Barberis D, Tamagnone L, Comoglio P M, Nat Cell Biol. 2002, 4(9):720-4; Conrotto P, Valdembri D, Corso S, Serini G, Tamagnone L, Comoglio P M, Bussolino F, Giordano S, Blood. 2005, 105(11):4321-9; Conrotto P, Corso S, Gamberini S, Comoglio P M, Giordano S, Oncogene. 2004, 23:5131-7] which may further add to the complexity of regulation of cell function by this receptor. Finally recent data demonstrate that cMet could be involved in tumor resistance to gefitinib or erlotinib suggesting that combination of compound targeting both EGFR and cMet might be of significant interest [Engelman J A at al., Science, 2007, 316:1039-43].

In the past few years, many different strategies have been developed to attenuate cMet signalling in cancer cell lines. These strategies include i) neutralizing antibodies against cMet or HGF/SF [Cao B, Su Y, Oskarsson M, Zhao P, Kort E J, Fisher R J, Wang L M, Vande Woude G F, Proc Natl Acad Sci USA. 2001, 98(13):7443-8; Martens T, Schmidt N O, Eckerich C, Fillbrandt R, Merchant M, Schwall R, Westphal M, Lamszus K, Clin Cancer Res. 2006, 12(20):6144-52] or the use of HGF/SF antagonist NK4 to prevent ligand binding to cMet [Kuba K, Matsumoto K, Date K, Shimura H, Tanaka M, Nakamura T, Cancer Res., 2000, 60:6737-43], ii) small ATP binding site inhibitors to cMet that block kinase activity [Christensen J G, Schreck R, Burrows J, Kuruganti P, Chan E, Le P, Chen J, Wang X, Ruslim L, Blake R, Lipson K E, Ramphal J, Do S, Cui J J, Chemington J M, Mendel D B, Cancer Res. 2003, 63:7345-55], iii) engineered SH2 domain polypeptide that interferes with access to the multidocking site and RNAi or ribozyme that reduce receptor or ligand expression. Most of these approaches display a selective inhibition of cMet resulting in tumor inhibition and showing that cMet could be of interest for therapeutic intervention in cancer.

The present invention aims to provide at least one reagent that can be used as a diagnostic or prognostic biomarker for detecting and/or monitoring oncogenic disorders especially those characterized by expression of cMet or those that are mediated by aberrant cMet expression.

Previous attempts to develop a valuable antibody that can be used as a diagnostic or prognostic tool have not been reported. Described herein are novel antibodies that meet this criteria.

Other features and advantages of the invention will be apparent from the detailed description and examples that follow.

In a first aspect, a subject of the invention is an isolated antibody, or one of its functional fragments or derivatives, that binds to the cMet receptor (cMet) preferably human cMet, with high affinity and can thus be useful in methods to diagnose pathological hyperproliferative oncogenic disorders mediated by cMet expression.

The expressions "functional fragment(s) and/or derivative(s)" will be defined in details later in the present specification.

It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described further on.

More particularly, according to another aspect of the invention, it is claimed an isolated antibody, or one of its functional fragments or derivatives, capable to bind specifically to cMet, said antibody being characterized in that it comprises at least one complementary determining region (CDR) chosen from CDRs comprising the amino acid sequence SEQ ID Nos. 1 to 12 or 29 to 39 or at least one CDR whose sequence has at least 80%, preferably 85%, 90%, 95% and 98% identity after optimal alignment with sequences 1 to 12 or 29 to 39.

A "functional fragment" of an antibody means in particular an antibody fragment, such as fragments Fv, scFv (sc=simple chain), Fab, F(ab')$_2$, Fab', scFv-Fc or diabodies, or any fragment whose half-life has been increased. Such functional fragments will be described in detail later in the present description.

A "derived compound" or "derivative" of an antibody means in particular a binding protein composed of a peptide scaffold and at least one of the CDRs of the original antibody in order to preserve its ability to be recognized. Such derived compounds, well-known to a person skilled in the art, will be described in more detail later in the present description.

More preferably, the invention comprises the antibodies, their derived compounds or their functional fragments, according to the present invention, obtained by genetic recombination or chemical synthesis.

According to a preferred embodiment, the antibody according to the invention, or its derived compounds or functional fragments, is characterized in that it consists of a monoclonal antibody.

"Monoclonal antibody" is understood to mean an antibody arising from a nearly homogeneous antibody population. More particularly, the individual antibodies of a population are identical except for a few possible naturally-occurring mutations which can be found in minimal proportions. In other words, a monoclonal antibody consists of a homogeneous antibody arising from the growth of a single cell clone (for example a hybridoma, a eukaryotic host cell transfected with a DNA molecule coding for the homogeneous antibody, a prokaryotic host cell transfected with a DNA molecule coding for the homogeneous antibody, etc.) and is generally characterized by heavy chains of one and only one class and subclass, and light chains of only one type. Monoclonal antibodies are highly specific and are directed against a single antigen. In addition, in contrast with preparations of polyclonal antibodies which typically include various antibodies directed against various determinants, or epitopes, each monoclonal antibody is directed against a single epitope of the antigen.

It must be understood here that the invention does not relate to antibodies in natural form, i.e., they are not taken from their natural environment but are isolated or obtained by purification from natural sources or obtained by genetic recombination or chemical synthesis and thus they can carry unnatural amino acids as will be described below.

In a first and preferred embodiment of the invention, the CDRs of the antibody will be defined according to the IMGT numbering system.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cystein 23 (1st-CYS), tryptophan 41 (CONSERVED-TRP), hydrophobic amino acid 89, cystein 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

Three heavy chain CDRs and 3 light chain CDRs exist. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

More particularly, according a first aspect, the invention relates to an isolated antibody, or a functional fragment or derivative thereof, capable of binding specifically to the c-Met protein, comprising i) a heavy chain comprising at least one of the following CDR-H1, CDR-H2 and CDR-H3, as defined according to IMGT numbering system, wherein CDR-H1 comprises the sequence SEQ ID No. 55, CDR-H2 comprises the sequence SEQ ID No. 56 and CDR-H3 comprises the sequence SEQ ID No. 57; and/or ii) a light chain comprising at least one of the following CDR-L1, CDR-L2 and CDR-L3, as defined according to IMGT numbering system, wherein CDR-L1 comprises the sequence SEQ ID No. 58, CDR-L2 comprises the sequence SEQ ID No. 59 and CDR-L3 comprises the sequence SEQ ID No. 60.

In a preferred embodiment, the present invention is directed to an isolated antibody, or a functional fragment or derivative thereof, capable of binding specifically to the c-Met protein, characterized in that it comprises i) a heavy chain comprising at least the following three CDRs CDR-H1, CDR-H2 and CDR-H3, as defined according to IMGT numbering system, wherein CDR-H1 comprises the sequence SEQ ID No. 55, CDR-H2 comprises the sequence SEQ ID No. 56 and CDR-H3 comprises the sequence SEQ ID No. 57; and/or ii) a light chain comprising at least the following three CDRs CDR-L1, CDR-L2 and CDR-L3, as defined according to IMGT numbering system, wherein CDR-L1 comprises the sequence SEQ ID No. 58, CDR-L2 comprises the sequence SEQ ID No. 59 and CDR-L3 comprises the sequence SEQ ID No. 60.

In order to clarify, the consensus sequences SEQ ID Nos. 55 to 60 of the invention are summarized in the following table 1.

TABLE 1

| | SEQ ID No. | Sequence (IMGT) |
|---|---|---|
| CDR-H1 | 55 | $GYX_1X_2TSX_3YX_4$ |
| CDR-H2 | 56 | $INX_5X_6X_7GX_8X_9$ |
| CDR-H3 | 57 | $X_{10}RX_{11}X_{12}X_{13}X_{14}X_{15}X_{16}X_{17}Y$ |
| CDR-L1 | 58 | $X_{18}X_{19}X_{29}X_{21}X_{22}Y$ |
| CDR-L2 | 59 | $X_{23}X_{24}S$ |
| CDR-L3 | 60 | $QQX_{25}NSX_{26}PX_{27}T$ |

With:
$X_1$: S or T    $X_2$: I or F    $X_3$: A or −    $X_4$: F or W
$X_5$: Y or P    $X_6$: D or S    $X_7$: − or N    $X_8$: T or R
$X_9$: N or T    $X_{10}$: T or A    $X_{11}$: D or R    $X_{12}$: R or V
$X_{13}$: T or G    $X_{14}$: F or Y    $X_{15}$: A or L    $X_{16}$: − or M
$X_{17}$: − or D    $X_{18}$: Q or −    $X_{19}$: R or S    $X_{20}$: I or S
$X_{21}$: Y or V    $X_{22}$: N or S    $X_{23}$: Y or D    $X_{24}$: A or T
$X_{25}$: S or W    $X_{26}$: W or N    $X_{27}$: L or P
"−" for "missing" (deletion of the amino acid residue at this position)

According to a particular embodiment, the antibody of the invention, or one of its functional fragments or derivatives, is characterized in that it comprises a heavy chain comprising the following three CDRs as defined according to IMGT, respectively CDR-H1, CDR-H2 and CDR-H3, wherein CDR-H1 comprises the sequence SEQ ID No. 7, CDR-H2 comprises the sequence SEQ ID No. 2 and CDR-H3 comprises the sequence SEQ ID No. 8.

According to a particular embodiment, the antibody of the invention, or one of its functional fragments or derivatives, is characterized in that it comprises a light chain comprising the following three CDRs as defined according to IMGT, respectively CDR-L1, CDR-L2 and CDR-L3, wherein CDR-L1 comprises the sequence SEQ ID No. 4, CDR-L2 comprises the sequence SEQ ID No. 5 and CDR-L3 comprises the sequence SEQ ID No. 6.

According to a particular embodiment, the antibody of the invention, or one of its functional fragments or derivatives, is characterized in that it comprises a heavy chain comprising the following three CDRs as defined according to IMGT numbering system, respectively CDR-H1, CDR-H2 and CDR-H3, wherein CDR-H1 comprises the sequence SEQ ID No. 29, CDR-H2 comprises the sequence SEQ ID No. 30 and CDR-H3 comprises the sequence SEQ ID No. 31.

According to a particular embodiment, the antibody of the invention, or one of its functional fragments or derivatives, is characterized in that it comprises a light chain comprising the following three CDRs as defined according to IMGT numbering system, respectively CDR-L1, CDR-L2 and CDR-L3, wherein CDR-L1 comprises the sequence SEQ ID No. 32, CDR-L2 comprises the sequence SEQ ID No. 33 and CDR-L3 comprises the sequence SEQ ID No. 34.

In other words, the invention can also be described as an antibody, or a functional fragment or derivative thereof, characterized in that it comprises a heavy chain selected from the group consisting of:
a) a heavy chain comprising the following three CDRs as defined according to IMGT numbering system, respectively CDR-H1 having the sequence SEQ ID No. 7, CDR-H2 having the sequence SEQ ID No. 2 and CDR-H3 having the sequence SEQ ID No. 8; and
b) a heavy chain comprising the following three CDRs as defined according to IMGT numbering system, respectively CDR-H1 having the sequence SEQ ID No. 29, CDR-H2 having the sequence SEQ ID No. 30 and CDR-H3 having the sequence SEQ ID No. 31.

The invention can also be described as an antibody, or a functional fragment or derivative thereof, characterized in that it comprises a light chain selected from the group consisting of:
a) a light chain comprising the following three CDRs as defined according to IMGT numbering system, respectively CDR-L1 having the sequence SEQ ID No. 4, CDR-L2 having the sequence SEQ ID No. 5 and CDR-L3 having the sequence SEQ ID No. 6; and
b) a light chain comprising the following three CDRs as defined according to IMGT numbering system, respectively CDR-L1 having the sequence SEQ ID No. 32, CDR-L2 having the sequence SEQ ID No. 33 and CDR-L3 having the sequence SEQ ID No. 34.

In another embodiment, complementarity-determining region, or CDR, means the hypervariable regions of the heavy and light chains of immunoglobulins as defined by Kabat et al. (Kabat et al., Sequences of proteins of immunological interest, 5$^{th}$ Ed., U.S. Department of Health and Human Services, NIH, 1991, and later editions). There are three heavy-chain CDRs and three light-chain CDRs. Here, the terms "CDR" and "CDRs" are used to indicate, depending on the case, one or more, or even all, of the regions containing the majority of the amino acid residues responsible for the antibody's binding affinity for the antigen or epitope it recognizes.

According to another particular embodiment, the antibody of the invention, or one of its functional fragments or derivatives, is characterized in that it comprises a heavy chain comprising the following three CDRs as defined according to Kabat, respectively CDR-H1, CDR-H2 and CDR-H3, wherein CDR-H1 comprises the sequence SEQ ID NO. 9, CDR-H2 comprises the sequence SEQ ID No. 10 and CDR-H3 comprises the sequence SEQ ID No. 3.

According to another particular embodiment, the antibody of the invention, or one of its functional fragments or derivatives, is characterized in that it comprises a light chain comprising the following three CDRs as defined according to Kabat, respectively CDR-L1, CDR-L2 and CDR-L3, wherein CDR-L1 comprises the sequence 11, CDR-L2 comprises the sequence 12 and CDR-L3 comprises the sequence 6.

According to another particular embodiment, the antibody of the invention, or one of its functional fragments or derivatives, is characterized in that it comprises a heavy chain comprising the following three CDRs as defined according to Kabat numbering system, respectively CDR-H1, CDR-H2 and CDR-H3, wherein CDR-H1 comprises the sequence SEQ ID NO. 35, CDR-H2 comprises the sequence SEQ ID No. 36 and CDR-H3 comprises the sequence SEQ ID No. 37.

According to another particular embodiment, the antibody of the invention, or one of its functional fragments or derivatives, is characterized in that it comprises a light chain comprising the following three CDRs as defined according to Kabat numbering system, respectively CDR-L1, CDR-L2 and CDR-L3, wherein CDR-L1 comprises the sequence SEQ ID No. 38, CDR-L2 comprises the sequence SEQ ID No. 39 and CDR-L3 comprises the sequence SEQ ID No. 34.

Another way to define the CDRs of the antibodies according to the invention can consist of determining the common residues for each CDR according to IMGT and to Kabat.

According to another embodiment, the antibody of the invention, or one of its functional fragments or derivatives, is characterized in that it comprises a heavy chain comprising at least one of the three CDRs of the sequences SEQ ID Nos. 1, 2 or 3, or at least one sequence with at least 80%, preferably 85%, 90%, 95% and 98% identity after optimal alignment with sequences SEQ ID Nos. 1, 2 or 3.

More particularly, the antibody of the invention, or one of its functional fragments or derivatives, is characterized in that it comprises a light chain comprising at least one of the three CDRs of the sequences SEQ ID Nos. 4, 5 or 6, or at least one sequence with at least 80%, preferably 85%, 90%, 95% and 98% identity after optimal alignment with sequences SEQ ID Nos. 4, 5 or 6.

In a preferred manner, the antibody of the invention, or one of its functional fragments or derivatives, is characterized in that it comprises a heavy chain comprising the following three CDRs, respectively CDR-H1, CDR-H2 and CDR-H3, wherein:
  CDR-H1 comprises the sequence SEQ ID No. 1, 7, 9, 29 or 35, or a sequence with at least 80%, preferably 85%, 90%, 95% and 98% identity after optimal alignment with sequence SEQ ID No. 1, 7, 9, 29 or 35;
  CDR-H2 comprises the sequences SEQ ID No. 2, 10, 30 or 36, or a sequence with at least 80%, preferably 85%, 90%, 95% and 98% identity after optimal alignment with sequence SEQ ID No. 2, 10, 30 or 36; and
  CDR-H3 comprises the sequence SEQ ID No. 3, 8, 31 or 37, or a sequence with at least 80%, preferably 85%, 90%, 95% and 98% identity after optimal alignment with sequence SEQ ID No. 3, 8, 31 or 37.

Even more preferably, the antibody of the invention, or one of its functional fragments or derivatives, is characterized in that it comprises a light chain comprising the following three CDRs, respectively CDR-L1, CDR-L2 and CDR-L3, wherein:
  CDR-L1 comprises the sequence SEQ ID No. 4, 11, 32 or 38, or a sequence with at least 80%, preferably 85%, 90%, 95% and 98% identity after optimal alignment with sequence SEQ ID No. 4, 11, 32 or 38;
  CDR-L2 comprises the sequences SEQ ID No. 5, 12, 33 or 39, or a sequence with at least 80%, preferably 85%, 90%, 95% and 98% identity after optimal alignment with sequence SEQ ID No. 5, 12, 33 or 39; and
  CDR-L3 comprises the sequence SEQ ID No. 6 or 34, or a sequence with at least 80%, preferably 85%, 90%, 95% and 98% identity after optimal alignment with sequence SEQ ID No. 6 or 34.

In still another embodiment, the invention can also be described as an antibody, or a functional fragment or derivative thereof, characterized in that it is selected from the group consisting of:
a) an antibody, or a functional fragment or derivative thereof, comprising:
  a heavy chain comprising the following three CDRs as defined according to IMGT, respectively CDR-H1 having the sequence SEQ ID No. 7, CDR-H2 having the sequence SEQ ID No. 2 and CDR-H3 having the sequence SEQ ID No. 8, and
  a light chain comprising the following three CDRs as defined according to IMGT, respectively CDR-L1 having the sequence SEQ ID No. 4, CDR-L2 having the sequence SEQ ID No. 5 and CDR-L3 having the sequence SEQ ID No. 6; and
b) an antibody, or a functional fragment or derivative thereof, comprising:
  a heavy chain comprising the following three CDRs as defined according to IMGT, respectively CDR-H1 having the sequence SEQ ID No. 29, CDR-H2 having the sequence SEQ ID No. 30 and CDR-H3 having the sequence SEQ ID No. 31; and
  a light chain comprising the following three CDRs as defined according to IMGT, respectively CDR-L1 having the sequence SEQ ID No. 32, CDR-L2 having the sequence SEQ ID No. 33 and CDR-L3 having the sequence SEQ ID No. 34.

In the present description, the terms "polypeptides", "polypeptide sequences", "peptides" and "proteins attached to antibody compounds or to their sequences" are interchangeable.

It must be understood here that the invention does not relate to antibodies in natural form, i.e., they are not taken from their natural environment but are isolated or obtained by purification from natural sources or obtained by genetic recombination or chemical synthesis and thus they can carry unnatural amino acids as will be described below.

For more clarity, it must be understood that in the following description, and more particularly in tables 3a and 4a, the CDRs of the antibody called 224D10, will be defined by IMGT numbering, kabat numbering and by common numbering.

Common numbering regroups the residues part of each CDR which are common to the CDRs as defined by the IMGT and the Kabat numbering systems.

IMGT numbering system defines the CDRs according to the IMGT system as defined whereas kabat numbering system defines the CDRs according to the kabat system as above defined.

More particularly, the CDR-H1 consists of the SEQ ID No. 1 (TSAYF) in the common numbering system, of SEQ ID No. 7 (GYSITSAYF) in the IMGT numbering system and of SEQ ID No. 9 (TSAYFWS) in the kabat numbering system.

The CDR-H2 consists of SEQ ID No. 2 (INYDGTN) in the common and IMGT numbering systems and of SEQ ID No. 10 (FINYDGTNNYNPSLKN) in the kabat numbering system.

The CDR-H3 consists in the SEQ ID No. 3 (DRTFAY) in the common and kabat numbering systems whereas it consists of SEQ ID No. 8 (TRDRTFAY) in the IMGT numbering system.

For the light chain, CDR-L1 consists of SEQ ID No. 4 (QRIYNY) in the common and IMGT numbering systems and of SEQ ID No. 11 (RASQRIYNYLH) in the kabat numbering system.

Concerning the CDR-L2, it consists of SEQ ID No. 5 (YAS) in the common and IMGT numbering systems and of SEQ ID No. 12 (YASQSIS) in the kabat numbering system.

At last, the CDR-L3 consists of SEQ ID No. 6 (QQSNSWPLT) for each of the three numbering systems.

The same can be easily done by the man skilled in the art for the antibody 221C9.

In parallel, for more clarity, it must be understood that in the following description, and more particularly in tables 3b and 4b, the CDRs of the antibody called 221C9, will be defined by IMGT numbering and by kabat numbering.

In the sense of the present invention, the "percentage identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P).

The percentage identity between two nucleic acid or amino acid sequences is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid or nucleotide residue is identical between the two sequences, dividing the number of identical positions by the total number of positions in the alignment window and multiplying the result by 100 to obtain the percentage identity between the two sequences.

For example, the BLAST program, "BLAST 2 sequences" (Tatusova et al., "Blast 2 sequences—a new tool for comparing protein and nucleotide sequences", FEMS Microbiol., 1999, Lett. 174:247-250) available on the site http://www.ncbi.nlm.nih.gov/gorf/b12.html, can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antibodies likely to be generated.

As a non-limiting example, table 2 below summarizes the possible substitutions likely to be carried out without resulting in a significant modification of the biological activity of the corresponding modified antibody; inverse substitutions are naturally possible under the same conditions.

TABLE 2

| Original residue | Substitution(s) |
| --- | --- |
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (G) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

It is known by those skilled in the art that in the current state of the art the greatest variability (length and composition) between the six CDRs is found at the three heavy-chain CDRs and, more particularly, at CDR-H3 of this heavy chain.

In a specific embodiment, the present invention relates to a murine antibody, or derived compounds or functional fragments of same.

Another embodiment of the invention discloses the antibody 224D10, or one of its functional fragments or derivatives, comprising a heavy chain comprising the following three
  CDRs, based on the "common" definition of the CDRs:
    CDR-H1 of the sequence SEQ ID No. 1 or of a sequence with at least 80%, preferably 85%, 90%, 95% and 98% identity after optimal alignment with sequence SEQ ID No. 1;
    CDR-H2 of the sequence SEQ ID No. 2 or of a sequence with at least 80%, preferably 85%, 90%, 95% and 98% identity after optimal alignment with sequence SEQ ID No. 2; and
    CDR-H3 of the sequence SEQ ID No. 3 or of a sequence with at least 80%, preferably 85%, 90%, 95% and 98% identity after optimal alignment with sequence SEQ ID No. 3, and
  a light chain comprising the following three CDRs:
    CDR-L1 of the sequence SEQ ID No. 4 or of a sequence with at least 80%, preferably 85%, 90%, 95% and 98% identity after optimal alignment with sequence SEQ ID No. 4;
    CDR-L2 of the sequence SEQ ID No. 5 or of a sequence with at least 80%, preferably 85%, 90%, 95% and 98% identity after optimal alignment with sequence SEQ ID No. 5; and
    CDR-L3 of the sequence SEQ ID No. 6 or of a sequence with at least 80%, preferably 85%, 90%, 95% and 98% identity after optimal alignment with sequence SEQ ID No. 6.

Still another embodiment of the invention discloses the antibody 224D10, or one of its functional fragments or derivatives, comprising a light chain comprising the following three CDRs, based on the IMGT numbering system:

CDR-H1 of the sequence SEQ ID No. 7 or of a sequence with at least 80%, preferably 85%, 90%, 95% and 98% identity after optimal alignment with sequence SEQ ID No. 7;

CDR-H2 of the sequence SEQ ID No. 2 or of a sequence with at least 80%, preferably 85%, 90%, 95% and 98% identity after optimal alignment with sequence SEQ ID No. 2; and CDR-H3 of the sequence SEQ ID No. 8 or of a sequence with at least 80%, preferably 85%, 90%, 95% and 98% identity after optimal alignment with sequence SEQ ID No. 8, and a light chain comprising the following three CDRs:

CDR-L1 of the sequence SEQ ID No. 4 or of a sequence with at least 80%, preferably 85%, 90%, 95% and 98% identity after optimal alignment with sequence SEQ ID No. 4;

CDR-L2 of the sequence SEQ ID No. 5 or of a sequence with at least 80%, preferably 85%, 90%, 95% and 98% identity after optimal alignment with sequence SEQ ID No. 5; and CDR-L3 of the sequence SEQ ID No. 6 or of a sequence with at least 80%, preferably 85%, 90%, 95% and 98% identity after optimal alignment with sequence SEQ ID No. 6.

Still another embodiment of the invention discloses the antibody 224D10, or one of its functional fragments or derivatives, comprising a heavy chain comprising the following three CDRs, based on the Kabat numbering system:

CDR-H1 of the sequence SEQ ID No. 9 or of a sequence with at least 80%, preferably 85%, 90%, 95% and 98% identity after optimal alignment with sequence SEQ ID No. 9;

CDR-H2 of the sequence SEQ ID No. 10 or of a sequence with at least 80%, preferably 85%, 90%, 95% and 98% identity after optimal alignment with sequence SEQ ID No. 10; and CDR-H3 of the sequence SEQ ID No. 3 or of a sequence with at least 80%, preferably 85%, 90%, 95% and 98% identity after optimal alignment with sequence SEQ ID No. 3, and a light chain comprising the following three CDRs:

CDR-L1 of the sequence SEQ ID No. 11 or of a sequence with at least 80%, preferably 85%, 90%, 95% and 98% identity after optimal alignment with sequence SEQ ID No. 11;

CDR-L2 of the sequence SEQ ID No. 12 or of a sequence with at least 80%, preferably 85%, 90%, 95% and 98% identity after optimal alignment with sequence SEQ ID No. 12; and CDR-L3 of the sequence SEQ ID No. 6 or of a sequence with at least 80%, preferably 85%, 90%, 95% and 98% identity after optimal alignment with sequence SEQ ID No. 6.

The antibody 224D10, or one of its functional fragments or derivatives, according to the invention is characterized in that it comprises, according to the "common" numbering system:

a heavy chain comprising the CDR-H1 of the sequence SEQ ID No. 1, the CDR-H2 of the sequence SEQ ID No. 2 and the CDR-H3 of the sequence SEQ ID No. 3; and a light chain comprising the CDR-L1 of the sequence SEQ ID No. 4, the CDR-L2 of the sequence SEQ ID No. 5 and the CDR-L3 of the sequence SEQ ID No. 6.

In another embodiment, the antibody 224D10, or one of its functional fragments or derivatives, according to the invention is characterized in that it comprises, according to the IMGT numbering system:

a heavy chain comprising the CDR-H1 of the sequence SEQ ID No. 7, the CDR-H2 of the sequence SEQ ID No. 2 and the CDR-H3 of the sequence SEQ ID No. 8; and a light chain comprising the CDR-L1 of the sequence SEQ ID No. 4, the CDR-L2 of the sequence SEQ ID No. 5 and the CDR-L3 of the sequence SEQ ID No. 6.

In another embodiment, the antibody 224D10, or one of its functional fragments or derivatives, according to the invention is characterized in that it comprises, according to the Kabat numbering system:

a heavy chain comprising the CDR-H1 of the sequence SEQ ID No. 9, the CDR-H2 of the sequence SEQ ID No. 10 and the CDR-H3 of the sequence SEQ ID No. 3; and a light chain comprising the CDR-L1 of the sequence SEQ ID No. 11, the CDR-L2 of the sequence SEQ ID No. 12 and the CDR-L3 of the sequence SEQ ID No. 6.

According to still another embodiment, the antibody 224D10 of the invention, or its derived compounds or functional fragments, is characterized in that it comprises a heavy-chain variable domain sequence comprising the amino acid sequence SEQ ID No. 13 or a sequence with at least 80%, preferably 85%, 90%, 95% and 98% identity after optimal alignment with sequence SEQ ID No. 13; and/or in that it comprises a light-chain variable domain sequence comprising the amino acid sequence SEQ ID No. 14 or a sequence with at least 80%, preferably 85%, 90%, 95% and 98% identity after optimal alignment with sequence SEQ ID No. 14.

More particularly, the antibody of the invention, its derived compounds or its functional fragments, comprises:

a) a heavy-chain sequence variable domain comprising a amino acid sequence having at least 80%, preferably 85%, 90%, 95% and 98% identity after optimal alignment with sequence SEQ ID No. 13 and/or a light-chain variable domain sequence having at least 80%, preferably 85%, 90%, 95% and 98% identity after optimal alignment with sequence SEQ ID No. 14; and b) are characterized in that said antibody, or a functional fragment or derivative thereof,
is capable of binding specifically to the c-Met protein, and, preferably
does not block the binding of the ligand HGF to the c-Met protein.

In another embodiment of the invention, it discloses the antibody 221C9, or one of its functional fragments or derivatives, comprising a heavy chain comprising the following three CDRs:

CDR-H1 of the sequence SEQ ID No. 29 or of a sequence with at least 80%, preferably 85%, 90%, 95% and 98% identity after optimal alignment with sequence SEQ ID No. 29;

CDR-H2 of the sequence SEQ ID No. 30 or of a sequence with at least 80%, preferably 85%, 90%, 95% and 98% identity after optimal alignment with sequence SEQ ID No. 30; and CDR-H3 of the sequence SEQ ID No. 31 or of a sequence with at least 80%, preferably 85%, 90%, 95% and 98% identity after optimal alignment with sequence SEQ ID No. 31, and a light chain comprising the following three CDRs:

CDR-L1 of the sequence SEQ ID No. 32 or of a sequence with at least 80%, preferably 85%, 90%, 95% and 98% identity after optimal alignment with sequence SEQ ID No. 32;

CDR-L2 of the sequence SEQ ID No. 33 or of a sequence with at least 80%, preferably 85%, 90%, 95% and 98% identity after optimal alignment with sequence SEQ ID No. 33; and CDR-L3 of the sequence SEQ ID No. 34 or of a sequence with at least 80%, preferably 85%, 90%, 95% and 98% identity after optimal alignment with sequence SEQ ID No. 34.

Still another embodiment of the invention discloses the antibody 221C9, or one of its functional fragments or derivatives, comprising a light chain comprising the following three CDRs:

CDR-H1 of the sequence SEQ ID No. 35 or of a sequence with at least 80%, preferably 85%, 90%, 95% and 98% identity after optimal alignment with sequence SEQ ID No. 35;

CDR-H2 of the sequence SEQ ID No. 36 or of a sequence with at least 80%, preferably 85%, 90%, 95% and 98% identity after optimal alignment with sequence SEQ ID No. 36; and CDR-H3 of the sequence SEQ ID No. 37 or of a sequence with at least 80%, preferably 85%, 90%, 95% and 98% identity after optimal alignment with sequence SEQ ID No. 37, and a light chain comprising the following three CDRs:

CDR-L1 of the sequence SEQ ID No. 38 or of a sequence with at least 80%, preferably 85%, 90%, 95% and 98% identity after optimal alignment with sequence SEQ ID No. 38;

CDR-L2 of the sequence SEQ ID No. 39 or of a sequence with at least 80%, preferably 85%, 90%, 95% and 98% identity after optimal alignment with sequence SEQ ID No. 39; and CDR-L3 of the sequence SEQ ID No. 34 or of a sequence with at least 80%, preferably 85%, 90%, 95% and 98% identity after optimal alignment with sequence SEQ ID No. 34.

In other words, the isolated antibody 221C9, or one of its functional fragments or derivatives, according to the invention is characterized in that it comprises, according to the IMGT numbering system:

a heavy chain comprising the CDR-H1 of the sequence SEQ ID No. 29, the CDR-H2 of the sequence SEQ ID No. 30 and the CDR-H3 of the sequence SEQ ID No. 31; and a light chain comprising the CDR-L1 of the sequence SEQ ID No. 32, the CDR-L2 of the sequence SEQ ID No. 33 and the CDR-L3 of the sequence SEQ ID No. 34.

In another embodiment, the isolated antibody 221C9, or one of its functional fragments or derivatives, according to the invention is characterized in that it comprises, according to the Kabat numbering system:

a heavy chain comprising the CDR-H1 of the sequence SEQ ID No. 35, the CDR-H2 of the sequence SEQ ID No. 36 and the CDR-H3 of the sequence SEQ ID No. 37; and a light chain comprising the CDR-L1 of the sequence SEQ ID No. 38, the CDR-L2 of the sequence SEQ ID No. 39 and the CDR-L3 of the sequence SEQ ID No. 34.

According to still another embodiment, the antibody 221C9 of the invention, or its derived compounds or functional fragments, is characterized in that it comprises a heavy-chain variable domain sequence comprising the amino acid sequence SEQ ID No. 40 or a sequence with at least 80%, preferably 85%, 90%, 95% and 98% identity after optimal alignment with sequence SEQ ID No. 40; and/or in that it comprises a light-chain variable domain sequence comprising the amino acid sequence SEQ ID No. 41 or a sequence with at least 80%, preferably 85%, 90%, 95% and 98% identity after optimal alignment with sequence SEQ ID No. 41.

More particularly, the antibody of the invention, its derived compounds or its functional fragments, comprises:

a) a heavy-chain variable domain sequence comprising a amino acid sequence having at least 80%, preferably 85%, 90%, 95% and 98% identity after optimal alignment with sequence SEQ ID No. 40 and/or a light-chain variable domain sequence having at least 80%, preferably 85%, 90%, 95% and 98% identity after optimal alignment with sequence SEQ ID No. 41; and b) are characterized in that said antibody, or a functional fragment or derivative thereof,
is capable of binding specifically to the c-Met protein, and, preferably
does not block the binding of the ligand HGF to the c-Met protein.

In other words, the invention can also be described as an antibody, or a functional fragment or derivative thereof, characterized in that it is selected from the group consisting of:

a) an antibody, or a functional fragment or derivative thereof, comprising a heavy chain variable domain of sequence comprising the amino acid sequence SEQ ID No. 13 and a light chain variable domain of sequence comprising the amino acid sequence SEQ ID No. 14; and b) an antibody, or a functional fragment or derivative thereof, comprising a heavy chain variable domain of sequence comprising the amino acid sequence SEQ ID No. 40 and a light chain variable domain of sequence comprising the amino acid sequence SEQ ID No. 41.

As seen above, the invention also relates to any compound derived from an antibody as described in the invention.

More particularly, the antibody of the invention, or its derived compounds or functional fragments, is characterized in that said derived compound consists of a binding protein comprising a peptide scaffold on which is grafted at least one CDR in such a way as to preserve all or part of the paratope recognition properties of the initial antibody.

One or more sequences among the six CDR sequences described in the present invention can also be present on the various immunoglobulin protein scaffolding. In this case, the protein sequence makes it possible to recreate a peptide skeleton favorable to the folding of the grafted CDRs, enabling them to preserve their paratope antigen-recognition properties.

Generally, a person skilled in the art knows how to determine the type of protein scaffold on which to graft at least one of the CDRs arising from the original antibody. More particularly, it is known that to be selected such scaffolds must meet the greatest number of criteria as follows (Skerra A., J. Mol. Recogn., 2000, 13:167-187):

good phylogenetic conservation;
known three-dimensional structure (as, for example, by crystallography, NMR spectroscopy or any other technique known to a person skilled in the art);
small size;
few or no post-transcriptional modifications; and/or
easy to produce, express and purify.

The origin of such protein scaffolds can be, but is not limited to, the structures selected among: fibronectin and preferentially fibronectin type III domain 10, lipocalin, anticalin (Skerra A., J. Biotechnol., 2001, 74(4):257-75), protein Z arising from domain B of protein A of *Staphylococcus aureus*, thioredoxin A or proteins with a repeated motif such as the "ankyrin repeat" (Kohl et al., PNAS, 2003, vol. 100, No. 4, 1700-1705), the "armadillo repeat", the "leucine-rich repeat" and the "tetratricopeptide repeat".

Scaffolds derived from toxins such as, for example, toxins from scorpions, insects, plants, mollusks, etc., and the protein inhibiters of neuronal NO synthase (PIN) should also be mentioned.

An example, in no way limiting, of such hybrid constructions, is the insertion of the CDR-H1 (heavy chain) of an anti-CD4 antibody, namely 13B8.2, in one of the loops in the PIN, the new binding protein thus obtained preserving the same binding properties as the original antibody (Bes et al., Biochem. Biophys. Res. Commun., 2006, 343(1), 334-344). On a purely illustrative basis, grafting the CDR-H3 (heavy chain) of an anti-lysozyme VHH antibody on one of the loops of neocarzinostatin (Nicaise et al., Protein Science, 2004, 13(7): 1882-1891) can also be mentioned.

Lastly, as described above, such peptide scaffolds can comprise from one to six CDRs arising from the original antibody. Preferably, but not being a requirement, a person skilled in the art will select at least one CDR from the heavy chain, the latter being known to be primarily responsible for the specificity of the antibody. The selection of one or more relevant CDRs is obvious to a person skilled in the art, who will then choose suitable known techniques (Bes et al., FEBS Letters 508, 2001, 67-74).

The present invention thus relates to an antibody, or its derived compounds or functional fragments, characterized in that the peptide scaffold is selected among proteins that are a) phylogenetically well preserved, b) of robust architecture, c) with a well-known 3-D molecular organization, d) of small size and/or e) comprising regions that can be modified by deletion and/or insertion without modifying stability properties.

According to a preferred embodiment, the antibody of the invention, or its derived compounds or functional fragments, is characterized in that said peptide scaffold is selected among i) scaffolds arising from fibronectin, preferentially fibronectin type 3 domain 10, lipocalin, anticalin, protein Z arising from domain B of protein A of Staphylococcus aureus, thioredoxin A or proteins with a repeated motif such as the "ankyrin repeat" (Kohl et al., PNAS, 2003, vol. 100, No. 4, 1700-1705), the "armadillo repeat", the "leucine-rich repeat" and the "tetratricopeptide repeat" or iii) protein inhibiters of neuronal NO synthase (PIN).

Another aspect of the invention relates to the functional fragments of the antibody described above.

More particularly, the invention targets an antibody, or its derived compounds or functional fragments, characterized in that said functional fragment is selected among the fragments Fv, Fab, (Fab)$_2$, Fab', scFv, scFv-Fc and diabodies, or any fragment whose half-life has been increased such as PEGylated fragments.

Such functional fragments of the antibody according to the invention consist, for example, of the fragments Fv, scFv (sc=simple chain), Fab, F(ab')$_2$, Fab', scFv-Fc or diabodies, or any fragment whose half-life has been increased by chemical modification, such as the addition of polyalkylene glycol such as polyethylene glycol (PEGylation) (PEGylated fragments are referred to as Fv-PEG, scFv-PEG, Fab-PEG, F(ab')$_2$-PEG and Fab'-PEG), or by incorporation in a liposome, microspheres or PLGA, said fragments possessing at least one of the characteristic CDRs of the invention which is notably capable of exerting in a general manner activity, even partial, of the antibody from which it arises.

Preferably, said functional fragments will comprise or include a partial sequence of the variable heavy or light chain of the antibody from which they are derived, said partial sequence being sufficient to retain the same binding specificity as the antibody from which it arises and sufficient affinity, preferably at least equal to 1/100, more preferably at least 1/10 of that of the antibody from which it arises.

Such a functional fragment will contain at least five amino acids, preferably 6, 7, 8, 10, 15, 25, 50 or 100 consecutive amino acids of the sequence of the antibody from which it arises.

Preferably, these functional fragments will be of the types Fv, scFv, Fab, F(ab')$_2$, F(ab'), scFv-Fc or diabodies, which generally have the same binding specificity as the antibody from which they result. According to the present invention, fragments of the antibody of the invention can be obtained from the antibodies described above by methods such as enzyme digestion, including pepsin or papain, and/or by cleavage of the disulfide bridges by chemical reduction. The antibody fragments can be also obtained by recombinant genetics techniques also known to a person skilled in the art or by peptide synthesis by means, for example, of automatic peptide synthesizers such as those sold by Applied BioSystems, etc.

For more clarity, table 3a below summarizes the various amino acid sequences corresponding to the antibody 224D10 of the invention.

TABLE 3a

| Antibody | CDR numbering | Heavy chain | Light chain | SEQ ID NO. |
|---|---|---|---|---|
| 224D10 | Common | CDR-H1 | | 1 |
| | | CDR-H2 | | 2 |
| | | CDR-H3 | | 3 |
| | | | CDR-L1 | 4 |
| | | | CDR-L2 | 5 |
| | | | CDR-L3 | 6 |
| | IMGT | CDR-H1 | | 7 |
| | | CDR-H2 | | 2 |
| | | CDR-H3 | | 8 |
| | | | CDR-L1 | 4 |
| | | | CDR-L2 | 5 |
| | | | CDR-L3 | 6 |
| | Kabat | CDR-H1 | | 9 |
| | | CDR-H2 | | 10 |
| | | CDR-H3 | | 3 |
| | | | CDR-L1 | 11 |
| | | | CDR-L2 | 12 |
| | | | CDR-L3 | 6 |
| | | Mu. variable domain | | 13 |
| | | | Mu. variable domain | 14 |

(wherein Mu. = murine)

For more clarity, table 3b below summarizes the various amino acid sequences corresponding to the antibody 221C9 of the invention.

TABLE 3b

| Antibody | CDR numbering | Heavy chain | Light chain | SEQ ID NO. |
|---|---|---|---|---|
| 221C9 | IMGT | CDR-H1 | | 29 |
| | | CDR-H2 | | 30 |
| | | CDR-H3 | | 31 |
| | | | CDR-L1 | 32 |
| | | | CDR-L2 | 33 |
| | | | CDR-L3 | 34 |
| | Kabat | CDR-H1 | | 35 |
| | | CDR-H2 | | 36 |
| | | CDR-H3 | | 37 |
| | | | CDR-L1 | 38 |
| | | | CDR-L2 | 39 |
| | | | CDR-L3 | 34 |
| | | Mu. variable domain | | 40 |
| | | | Mu. variable domain | 41 |

(wherein Mu. = murine)

According to another aspect, the invention relates to a murine hybridoma capable of secreting a monoclonal antibody according to the invention, notably the hybridoma of murine origin deposited at the Collection Nationale de Cultures de Microorganismes (CNCM), Institut Pasteur, 28, rue du Dr. Roux, 75724, Paris, Cédex 15, France, on Mar. 12, 2008, under the number 1-3949. Said hybridoma was obtained by the fusion of Balb/C immunized mice splenocytes and cells of the myeloma Sp 2/0-Ag 14 lines.

The monoclonal antibody, here referred to as 224D10, or its derived compounds or functional fragments, characterized in that said antibody is secreted by the hybridoma deposited at the CNCM on Mar. 12, 2008, under number 1-3949 obviously forms part of the present invention.

According to another aspect, the invention relates to a murine hybridoma capable of secreting a monoclonal antibody according to the invention, notably the hybridoma of murine origin deposited at the Collection Nationale de Cultures de Microorganismes (CNCM), Institut Pasteur, 28, rue du Dr. Roux, 75724, Paris, Cédex 15, France, on Jan. 14, 2010, under the number 1-4273. Said hybridoma was obtained by the fusion of Balb/C immunized mice splenocytes and cells of the myeloma Sp 2/0-Ag 14 lines.

The monoclonal antibody, here referred to as 221C9, or its derived compounds or functional fragments, characterized in that said antibody is secreted by the hybridoma deposited at the CNCM on Jan. 14, 2010, under number 1-4273 obviously forms part of the present invention.

A novel aspect of the present invention relates to an isolated nucleic acid, characterized in that it is chosen from the following nucleic acids:
a) a nucleic acid, DNA or RNA, coding for an antibody or for a derived compound or functional fragment thereof, according to the invention;
b) a nucleic acid comprising a DNA sequence comprising a sequence selected from the group consisting of the sequences SEQ ID No. 15 to 26 and 42 to 52, or a sequence with at least 80%, preferably 85%, 90%, 95% and 98% identity after optimal alignment with the sequences SEQ ID 15 to 26 and 42 to 52;
c) a nucleic acid comprising a DNA sequence comprising the sequences SEQ ID No. 27, 28, 53 and/or 54 or a sequence with at least 80%, preferably 85%, 90%, 95% and 98% identity after optimal alignment with sequences SEQ ID 27, 28, 53 and/or 54;
d) the corresponding RNA nucleic acids of the nucleic acids as defined in a), b) or c);
e) the complementary nucleic acids of the nucleic acids as defined in a), b) and c); and
f) a nucleic acid of at least 18 nucleotides capable of hybridizing under conditions of high stringency with at least one of the CDRs of sequence SEQ ID No. 15 to 28 and 42 to 54 or a sequence with at least 80%, preferably 85%, 90%, 95% and 98% identity after optimal alignment with sequences SEQ ID 15 to 28 and 42 to 54, or a complementary sequence thereof.

Table 4a below summarizes the various nucleotide sequences concerning the antibody 224D10 of the invention.

TABLE 4a

| Antibody | CDR numbering | Heavy chain | Light chain | SEQ ID NO. |
|---|---|---|---|---|
| 224D10 | Common | CDR-H1 | | 15 |
| | | CDR-H2 | | 16 |
| | | CDR-H3 | | 17 |
| | | | CDR-L1 | 18 |
| | | | CDR-L2 | 19 |
| | | | CDR-L3 | 20 |

TABLE 4a-continued

| Antibody | CDR numbering | Heavy chain | Light chain | SEQ ID NO. |
|---|---|---|---|---|
| | IMGT | CDR-H1 | | 21 |
| | | CDR-H2 | | 16 |
| | | CDR-H3 | | 22 |
| | | | CDR-L1 | 18 |
| | | | CDR-L2 | 19 |
| | | | CDR-L3 | 20 |
| | Kabat | CDR-H1 | | 23 |
| | | CDR-H2 | | 24 |
| | | CDR-H3 | | 17 |
| | | | CDR-L1 | 25 |
| | | | CDR-L2 | 26 |
| | | | CDR-L3 | 20 |
| | | Mu. variable domain | | 27 |
| | | | Mu. variable domain | 28 |

Table 4b below summarizes the various nucleotide sequences concerning the antibody 221C9 of the invention.

TABLE 4b

| Antibody | CDR numbering | Heavy chain | Light chain | SEQ ID NO. |
|---|---|---|---|---|
| 221C9 | IMGT | CDR-H1 | | 42 |
| | | CDR-H2 | | 43 |
| | | CDR-H3 | | 44 |
| | | | CDR-L1 | 45 |
| | | | CDR-L2 | 46 |
| | | | CDR-L3 | 47 |
| | Kabat | CDR-H1 | | 48 |
| | | CDR-H2 | | 49 |
| | | CDR-H3 | | 50 |
| | | | CDR-L1 | 51 |
| | | | CDR-L2 | 52 |
| | | | CDR-L3 | 47 |
| | | Mu. variable domain | | 53 |
| | | | Mu. variable domain | 54 |

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, defining a fragment or a region of a nucleic acid, containing unnatural nucleotides or not, and being either a double-strand DNA, a single-strand DNA or transcription products of said DNAs.

It should also be included here that the present invention does not relate to nucleotide sequences in their natural chromosomal environment, i.e., in a natural state. The sequences of the present invention have been isolated and/or purified, i.e., they were sampled directly or indirectly, for example by a copy, their environment having been at least partially modified. Isolated nucleic acids obtained by recombinant genetics, by means, for example, of host cells, or obtained by chemical synthesis should also be mentioned here.

"Nucleic sequences exhibiting a percentage identity of at least 80%, preferably 85%, 90%, 95% and 98%, after optimal alignment with a preferred sequence" means nucleic sequences exhibiting, with respect to the reference nucleic sequence, certain modifications such as, in particular, a deletion, a truncation, an extension, a chimeric fusion and/or a substitution, notably punctual. Preferably, these are sequences which code for the same amino acid sequences as the reference sequence, this being related to the degeneration of the genetic code, or complementarity sequences that are likely to hybridize specifically with the reference sequences, preferably under highly stringent conditions, notably those defined below.

Hybridization under highly stringent conditions means that conditions related to temperature and ionic strength are selected in such a way that they allow hybridization to be maintained between two complementarity DNA fragments. On a purely illustrative basis, the highly stringent conditions of the hybridization step for the purpose of defining the polynucleotide fragments described above are advantageously as follows.

DNA-DNA or DNA-RNA hybridization is carried out in two steps: (1) prehybridization at 42° C. for three hours in phosphate buffer (20 mM, pH 7.5) containing 5×SSC (1×SSC corresponds to a solution of 0.15 M NaCl+0.015 M sodium citrate), 50% formamide, 7% sodium dodecyl sulfate (SDS), 10× Denhardt's, 5% dextran sulfate and 1% salmon sperm DNA; (2) primary hybridization for 20 hours at a temperature depending on the length of the probe (i.e.: 42° C. for a probe >100 nucleotides in length) followed by two 20-minute washings at 20° C. in 2×SSC+2% SDS, one 20-minute washing at 20° C. in 0.1×SSC+0.1% SDS. The last washing is carried out in 0.1×SSC+0.1% SDS for 30 minutes at 60° C. for a probe >100 nucleotides in length. The highly stringent hybridization conditions described above for a polynucleotide of defined size can be adapted by a person skilled in the art for longer or shorter oligonucleotides, according to the procedures described in Sambrook, et al. (Molecular cloning: a laboratory manual, Cold Spring Harbor Laboratory; 3rd edition, 2001).

The invention also relates to a vector comprising a nucleic acid as described in the invention.

The invention notably targets cloning and/or expression vectors that contain such a nucleotide sequence.

The vectors of the invention preferably contain elements which allow the expression and/or the secretion of nucleotide sequences in a given host cell. The vector thus must contain a promoter, translation initiation and termination signals, as well as suitable transcription regulation regions. It must be able to be maintained in a stable manner in the host cell and may optionally have specific signals which specify secretion of the translated protein. These various elements are selected and optimized by a person skilled in the art according to the host cell used. For this purpose, the nucleotide sequences can be inserted in self-replicating vectors within the chosen host or be integrative vectors of the chosen host.

Such vectors are prepared by methods typically used by a person skilled in the art and the resulting clones can be introduced into a suitable host by standard methods such as lipofection, electroporation, heat shock or chemical methods.

The vectors are, for example, vectors of plasmid or viral origin. They are used to transform host cells in order to clone or express the nucleotide sequences of the invention.

The invention also comprises host cells transformed by or comprising a vector as described in the present invention.

The host cell can be selected among prokaryotic or eukaryotic systems such as bacterial cells, for example, but also yeast cells or animal cells, notably mammal cells. Insect or plant cells can also be used.

The invention also relates to animals, other than man, that have a transformed cell according to the invention.

Another aspect of the invention relates to a method for the production of an antibody according to the invention, or one of its functional fragments, characterized in that said method comprises the following steps:

a) the culture in a medium of and the suitable culture conditions for a host cell according to the invention; and b) the recovery of said antibody, or one of its functional fragments, thus produced from the culture medium or from said cultured cells.

The transformed cells according to the invention are of use in methods for the preparation of recombinant polypeptides according to the invention. Methods for the preparation of polypeptide according to the invention in recombinant form, characterized in that said methods use a vector and/or a cell transformed by a vector according to the invention, are also comprised in the present invention. Preferably, a cell transformed by a vector according to the invention is cultured under conditions that allow the expression of the aforesaid polypeptide and recovery of said recombinant peptide.

As already mentioned, the host cell can be selected among prokaryotic or eukaryotic systems. In particular, it is possible to identify the nucleotide sequences of the invention that facilitate secretion in such a prokaryotic or eukaryotic system. A vector according to the invention carrying such a sequence can thus be used advantageously for the production of recombinant proteins to be secreted. Indeed, the purification of these recombinant proteins of interest will be facilitated by the fact that they are present in the supernatant of the cellular culture rather than inside host cells.

The polypeptides of the invention can also be prepared by chemical synthesis. One such method of preparation is also an object of the invention. A person skilled in the art knows methods for chemical synthesis, such as solid-phase techniques (see notably Steward et al., 1984, Solid phase peptides synthesis, Pierce Chem. Company, Rockford, Ill., 2nd ed.) or partial solid-phase techniques, by condensation of fragments or by conventional synthesis in solution. Polypeptides obtained by chemical synthesis and capable of containing corresponding unnatural amino acids are also comprised in the invention. The antibodies, or the derived compounds or functional fragments of same, likely to be obtained by the method of the invention are also comprised in the present invention.

The use of the antibody of the invention as biomarker is also disclosed. The methods may be used for detecting or diagnosing various hyperproliferative oncogenic disorders associated with expression of cMet exemplified by, but not limited to, prostate cancer, osteosarcomas, lung cancer, breast cancer, endometrial cancer, glioblastoma, colon, cancer, gastric cancer, renal cancer or any other cancer associated with expression of cMet. As would be recognized by one of ordinary skill in this art, the level of antibody expression associated with a particular disorder will vary depending on the nature and/or the severity of the pre-existing condition.

Administration of the antibodies of the present invention in any of the conventional ways known to one skilled in the art (e.g., topical, parenteral, intramuscular, etc.), will provide an extremely useful method of detecting dysplastic cells in a sample as well as allowing a clinician to monitor the therapeutic regiment of a patient undergoing treatment for a hyperproliferative disorder associated with or mediated by expression of cMet.

In another embodiment, the invention relates to a pharmaceutical composition for in vivo imaging of an oncogenic disorder associated with expression of cMet comprising the above monoclonal antibody or fragment thereof which is labeled and which binds cMet in vivo; and a pharmaceutically acceptable carrier.

The antibody of the invention, or a functional fragment or derivative thereof, will find use in various medical or research purposes, including the detection, diagnosis, and staging of various pathologies associated with expression of cMet.

Stage determination has potential prognostic value and provides criteria for designing optimal therapy. Simpson et al., J. Clin. Oncology 18:2059 (2000). Generally, pathological staging of breast cancer for example, is preferable to clinical staging because the former gives a more accurate prognosis. However, clinical staging would be preferred if it were as accurate as pathological staging because it does not depend on an invasive procedure to obtain tissue for pathological evaluation.

When used with suitable labels or other appropriate detectable biomolecule or chemicals, the antibody of the invention is particularly useful for in vitro and in vivo diagnostic and prognostic applications.

Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA). Various types of labels and methods of conjugating the labels to the antibodies of the invention are well known to those skilled in the art, such as the ones set forth below.

As used herein, the term "an oncogenic disorder associated with expression of cMet" is intended to include diseases and other disorders in which the presence of high levels or abnormally low levels of cMet (aberrant) in a subject suffering from the disorder has been shown to be or is suspected of being either responsible for the pathophysiology of the disorder or a factor that contributes to a worsening of the disorder. Alternatively, such disorders may be evidenced, for example, by an increase in the levels of cMet on the cell surface or in increased tyrosine autophosphorylation cMet in the affected cells or tissues of a subject suffering from the disorder. The increase in cMet levels may be detected, for example, using the antibody 224D10 of the invention. More, it refers to cells which exhibit relatively autonomous growth, so that they exhibit an aberrant growth phenotype characterized by a significant loss of control of cell proliferation. Alternatively, the cells may express normal levels of cMet but are marked by abnormal proliferation.

In certain embodiments, "increased expression" as it relates to cMet refers to protein or gene expression levels that demonstrate a statistically significant increase in expression (as measured by RNA expression or protein expression) relative to a control.

More particularly, it is considered the use of an antibody, or a functional fragment or derivative thereof, according to the invention as described, for diagnosing in vitro an oncogenic disorder associated with expression of cMet or determining in vitro the prognosis for developing an oncogenic disorder associated with expression of cMet, for example a cancer associated with expression of cMet.

Another broad aspect in accordance with the invention concerns a method of diagnosing pathological hyperproliferative oncogenic disorder or a susceptibility to a pathological condition associated with expression of cMet in a subject comprising determining the presence or absence of cMet bearing cells in a sample, and diagnosing a pathological condition or susceptibility to a pathological condition based on the presence or absence of said cMet bearing cells. The diagnostic uses of the antibody of the invention comprise primary tumors, cancers metastases. The antibody can be present in the form of an immunoconjugate or of a labeled antibody as to obtain a detectable and/or quantifiable signal.

More particularly, an preferred subject in accordance with the invention is a process of detecting in vitro the presence and/or the location of a cMet expressing tumor in a subject, wherein said process comprises the steps of (a) contacting a sample from the subject with an antibody, or a functional fragment or derivative thereof, according to the invention, and (b) detecting the binding of said antibody with the sample. Another aspect of the subject is the follow-up of c-Met expression as a response to a c-Met targeted therapy during clinical trials, and more particularly when the downregulation and or degradation of the c-Met receptor is one of the component of the mechanism of action of the tested compound.

As will be apparent to the skilled artisan, the detection of the binding of the antibody of the invention may be revealed by various assays. Although any means for carrying out the assays is compatible with the invention, it can be mentioned, as examples, FACS, ELISA or IHC.

As used herein, the term "sample" is intended to mean any biological fluid, cell, tissue, organ or portion thereof, that includes or potentially includes a neoplastic cell, such as a cell from the colon, gastric, rectum, breast, ovary, prostate, kidney, lung, blood, brain or other organ or tissue that contains or is suspected to contain a neoplastic cell. The term includes samples present in an individual as well as samples obtained or derived from the individual. For example, a sample can be a histologic section of a specimen obtained by biopsy, or cells that are placed in or adapted to tissue culture. A sample further can be a subcellular fraction or extract, or a crude or substantially pure nucleic acid molecule or protein preparation.

Clinical sample is intended to encompass a variety of sample types obtained from a subject and useful in the procedure of the invention, such as for example, a diagnostic or monitoring test of determining or detecting cMet expression levels. The definition encompasses solid tissue samples obtained by surgical removal, a pathology specimen, an archived sample, or a biopsy specimen, tissue cultures or cells derived therefrom and the progeny thereof, and sections or smears prepared from any of these sources. Non-limiting examples are samples obtained from breast tissue, lymph nodes, colon, pancreas, prostate etc. The definition also encompasses liquid samples of biologic origin, and may refer to either the cells or cell fragments suspended therein, or to the liquid medium and its solutes.

Another aspect in accordance with the invention relates to a process of determining in vitro the expression level of cMet in a cMet expressing tumor from a subject, wherein said process comprises the steps of (a') contacting a sample from the subject with an antibody, or a functional fragment or derivative thereof, according to the invention, and (b') quantifying the level of antibody binding to cMet in said sample.

As will be apparent to the skilled artisan, the level of antibody binding to cMet may be quantified in a number of ways such as by various assays. Although any means for carrying out the assays is compatible with the invention, a preferred method brings into play immunoenzymatic processes according to the ELISA technique, by immuno fluorescence, by immunohistochemistry or radio-immunoassay (RIA) technique or equivalent.

Preferably, the biological sample is formed by a biological fluid, such as serum, whole blood, cells, a tissue sample or biopsies of human origin. The sample, may for example include, biopsied tissue, which can be conveniently assayed for the presence of a pathological hyperproliferative oncogenic disorder associated with expression of cMet.

Once a determination is made of the amount of cMet present in the test sample, the results can be compared with those of control samples, which are obtained in a manner similar to the test samples but from individuals that do not have or present with a hyperproliferative oncogenic disorder associated with expression of cMet. If the level of the cMet is significantly elevated in the test sample, it may be concluded that there is an increased likelihood of the subject from which it was derived has or will develop said disorder.

The invention relates, more particularly, to a process of diagnosing in vitro a cMet expressing tumor or determining in vitro the prognosis for developing a cMet expressing tumor in a subject, wherein said process comprises the steps of (i) determining the expression level of cMet as above described, and (ii) comparing the expression level of step (i) with a reference expression level of cMet from normal tissue or a non expressing cMet tissue.

"Diagnosing" a disease as used in the application is intended to include, for example, diagnosing or detecting the presence of a pathological hyperproliferative oncogenic disorder associated with or mediated by expression of cMet, monitoring the progression of the disease, and identifying or detecting cells or samples that are indicative of a disorder associated with the expression of cMet.

"Prognosis" as used in this application means the likelihood of recovery from a disease or the prediction of the probable development or outcome of a disease. For example, if a sample from a subject is positive for staining with the antibody of the invention, then the "prognosis" for that subject is better than if the sample was negative for cMet staining. Samples may be scored for cMet expression levels on an appropriate scale as it will be more detailed hereinafter.

However another aspect of the invention is also related to the monitoring of c-Met expression for therapeutic compounds that induce a degradation of c-Met as one of their mechanisms of action. In that case following c-Met expression on cell membrane could be a critical tool to evaluate the efficacy of the treatment during clinical trials and "personalized" therapies.

The expression level of cMet is advantageously compared or measured in relation to levels in a control cell or sample also referred to as a "reference level" or "reference expression level". "Reference level", "reference expression level", "control level" and "control" are used interchangeably in the specification. Broadly speaking, a "control level" means a separate baseline level measured in a comparable control cell, which is generally disease or cancer free. It may be from the same individual or from another individual who is normal or does not present with the same disease from which the diseased or test sample is obtained. Within the context of the present invention, the term "reference level" refers to a "control level" of expression of cMet used to evaluate a test level of expression of cMet in a cancer cell-containing sample of a patient. For example, when the level of cMet in the biological sample of a patient are higher than the reference level of cMet, the cells will be considered to have a high level of expression, or overexpression, of cMet. The reference level can be determined by a plurality of methods. Expression levels may thus define cMet bearing cells or alternatively the level of expression of cMet independent of the number of cells expressing cMet. Thus the reference level for each patient can be proscribed by a reference ratio of cMet, wherein the reference ratio can be determined by any of the methods for determining the reference levels described herein.

For example, the control may be a predetermined value, which can take a variety of forms. It can be a single cut-off value, such as a median or mean. The "reference level" can be a single number, equally applicable to every patient individually, or the reference level can vary, according to specific subpopulations of patients. Thus, for example, older men might have a different reference level than younger men for the same cancer, and women might have a different reference level than men for the same cancer. Alternatively, the "reference level" can be determined by measuring the level of expression of cMet in non-oncogenic cancer cells from the same tissue as the tissue of the neoplastic cells to be tested. As well, the "reference level" might be a certain ratio of cMet in the neoplastic cells of a patient relative to the cMet levels in non-tumor cells within the same patient. The "reference level" can also be a level of cMet of in vitro cultured cells, which can be manipulated to simulate tumor cells, or can be manipulated in any other manner which yields expression levels which accurately determine the reference level. On the other hand, the "reference level" can be established based upon comparative groups, such as in groups not having elevated cMet levels and groups having elevated cMet levels. Another example of comparative groups would be groups having a particular disease, condition or symptoms and groups without the disease. The predetermined value can be arranged, for example, where a tested population is divided equally (or unequally) into groups, such as a low-risk group, a medium-risk group and a high-risk group or into quandrants or quintiles, the lowest quandrant or quintile being individuals with the lowest risk or highest amount of cMet and the highest quandrant or quintile being individuals with the highest risk or lowest amount of cMet.

The reference level can also be determined by comparison of the level of cMet in populations of patients having the same cancer. This can be accomplished, for example, by histogram analysis, in which an entire cohort of patients are graphically presented, wherein a first axis represents the level of cMet, and a second axis represents the number of patients in the cohort whose tumoral cells express cMet at a given level. Two or more separate groups of patients can be determined by identification of subsets populations of the cohort which have the same or similar levels of cMet. Determination of the reference level can then be made based on a level which best distinguishes these separate groups. A reference level also can represent the levels of two or more markers, one of which is cMet. Two or more markers can be represented, for example, by a ratio of values for levels of each marker.

Likewise, an apparently healthy population will have a different 'normal' range than will have a population which is known to have a condition associated with expression of cMet. Accordingly, the predetermined value selected may take into account the category in which an individual falls. Appropriate ranges and categories can be selected with no more than routine experimentation by those of ordinary skill in the art. By "elevated" "increased" it is meant high relative to a selected control. Typically the control will be based on apparently healthy normal individuals in an appropriate age bracket.

It will also be understood that the controls according to the invention may be, in addition to predetermined values, samples of materials tested in parallel with the experimental materials. Examples include tissue or cells obtained at the same time from the same subject, for example, parts of a single biopsy, or parts of a single cell sample from the subject.

In the clinical diagnosis or monitoring of patients with an cMet mediated diseases, the detection of cMet expressing cells or an increase in the levels of cMet, in comparison to the levels in a corresponding biological sample from a normal subject or non-cancerous tissue is generally indicative of a patient with or suspected of presenting with an cMet mediated disorder.

In accordance with the above, the invention provides for a method for predicting susceptibility to cancer comprising detecting the expression level of cMet in a tissue sample, its presence indicating susceptibility to cancer, wherein the degree of cMet expression correlates to the degree of susceptibility. Thus, in specific embodiments, the expression of cMet in, for example, prostate tissue, osteosarcomas tissue, lung tissue, pancreatic tissue, colon tissue, breast tissue, glyoblastoma tissue, ovarian tissues, or any other tissue suspected of cells expressing cMet is examined, with the presence of cMet in the sample providing an indication of cancer susceptibility or the emergence or existence of a tissue specific tumor.

A method for evaluating tumor aggressiveness is also provided. In one embodiment, a method for observing the progression of a malignancy in an individual over time comprises determining the level of cMet expressed by cells in a sample of the tumor, comparing the level so determined to the level of cMet expressed in an equivalent tissue sample taken from the same individual at a different time, wherein the degree of cMet expression in the tumor sample over time provides information on the progression of the cancer.

In yet another embodiment, the application provides methods for determining the appropriate therapeutic protocol for a subject. Specifically, the antibodies of the invention will be very useful for monitoring the course of amelioration of malignancy in an individual, especially in those circumstances where the subject is being treated with a cMet antibody that does not compete with the antibodies of the invention for binding to cMet. The presence or absence or a change in the level of cMet in accordance with the invention may be indicative that the subject is likely to have a relapse or a progressive, or a persistent cancer associated with cMet. Thus, by measuring an increase in the number of cells expressing cMet or changes in the concentration of cMet present in various tissues or cells, it is possible to determine whether a particular therapeutic regimen aimed at ameliorating a malignancy associated with cMet is effective.

Another subject of the invention is an in vivo method of imaging an oncogenic disorder associated with expression of cMet. For example, such a method can be used on a patient presenting symptoms of an oncogenic disorder. If the patient has, for example increased expression levels of cMet, then the patient is likely suffering from a cancerous disorder. As well, the method can be useful for monitoring progression and/or response to treatment in patients who have been previously diagnosed with a cMet mediated cancer. In accordance with the above objective, the invention provides an in vivo imaging reagent comprising an antibody according to the invention, or a functional fragment or derivative thereof, preferably labeled, especially radiolabeled, and its use in medical imaging. Thus, a general method in accordance with the invention works by administering to a patient an imaging-effective amount of an imaging reagent such as the above described monoclonal antibody which is labeled and a pharmaceutically effective carrier and then detecting the agent after it has bound to cMet present in the sample. In certain embodiments, the method works by administering an imaging-effective amount of an imaging agent comprising a targeting moiety and an active moiety. The imaging agent is administered in an amount effective for diagnostic use in a mammal such as a human and the localization and accumulation of the imaging agent is then detected. The localization and accumulation of the imaging agent may be detected by radionuclide imaging, radioscintigraphy, nuclear magnetic resonance imaging, computed tomography, positron emission tomography, computerized axial tomography, X-ray or magnetic resonance imaging method, fluorescence detection, and chemiluminescent detection.

In regards to the development of targeted antitumoral therapy, the diagnosis with immunohistological techniques gives, in situ, information on the receptor expression level and thus enable to select patients susceptible to be treated following the expression level of receptors needed for such a treatment.

For immunotherapy using monoclonal antibodies, the response to the treatment depending of the receptor targeted expression level as treatment with trastuzumab where determination of Her2 overexpression in breast carcinoma is now of major clinical importance with the advent of the humanised anti-Her2 monoclonal antibody trastuzumab. Demonstration of Her2 overexpression is a prerequisite for treatment with trastuzumab as it acts by specifically targeting Her2 overexpressing carcinoma cells. Accurate testing for Her2 aims to ensure that costly and potentially toxic trastuzumab treatment is not given to patients with non-overexpessing tumours and that every patient who might benefit from trastuzumab receives appropriate treatment.

The teaching with trastuzumab concerning the patient selection that overexpressed Her2 showed the benefit to determine the expression level of receptor when using a therapy with a monoclonal antibody and to develop, in the same time than a therapeutic monoclonal antibody, a monoclonal antibody which can be used for the patient selection.

As a consequence, the invention relates to a process of determining in vitro the cMet status of a tumor of a subject, wherein said process comprises the steps of (1) determining the expression level of cMet as above described, (2) scoring said tumor for cMet expression level, and (3) comparing said scoring to that obtained from a control sample.

"cMet status" within the meaning of the invention, relates to the classification of tumor to a cMet positive [cMet(+)] or cMet negative [cMet(−)] class based on the determination of the expression level of the cMet gene as measured by any methods such as immunohistochemistry (IHC), fluorescence in situ hybridization (FISH), colorimetric in situ hybridization (CISH), gene chip or other methods known by the man skilled in the art.

In a preferred embodiment, the antibody for diagnostic have to be to able to bind the targeted receptor when tissue samples are formalin fixed and paraffin embedded.

More particularly, the cMet expression level is measured by immunohistochemistry (IHC).

As an example, samples may be scored for cMet expression levels on a scale from 0-3$^+$ for levels of antibody staining, where 0 is negative and 1$^+$-3$^+$ represents positive staining at four semiquantitative steps of increasing intensity. Scores 1$^+$-3$^+$ can be recoded as positive because each positive score may be associated with significantly reduced risk for relapse and fatal disease when compared to score 0 (negative), but increasing intensity among the positive scores may provide additional risk reduction. Any conventional hazard analysis method may be used to estimate the prognostic value of cMet. Representative analysis methods include Cox regression analysis, which is a semiparametric method for modeling survival or time-to-event data in the presence of censored cases (Hosmer and Lemeshow, 1999; Cox, 1972). In contrast to other survival analyses, e.g. Life Tables or Kaplan-Meyer, Cox allows the inclusion of predictor variables (covariates) in the models. Using a convention analysis method, e.g., Cox one may be able to test hypotheses regarding the correlation of cMet expression status of in a primary tumor to time-to-onset of either disease relapse (disease-free survival time, or time to metastatic disease), or time to death from the disease (overall survival time). Cox regression analysis is also known as Cox proportional hazard analysis. This method is standard for testing the prognostic value of a tumor marker on patient survival time. When used in multivariate mode, the effect of several covariates are tested in parallel so that individual covariates that have independent prognostic value can be identified, i.e. the most useful markers. The term positive or negative "cMet status" [also referred as cMet(+) or cMet (−)] of tumors refers to scores 0 or scores $1^+$-$3^+$, respectively.

A sample may be "scored" during the diagnosis or monitoring of cancer, such as for example breast cancer. In its simplest form, scoring may be categorical negative or positive as judged by visual examination of samples by immunohistochemistry. More quantitative scoring involves judging the two parameters intensity of staining and the proportion of stained ("positive") cells that are sampled. Based on these two parameters numbers may be assigned that reflect increasing levels of positive staining Allred et al. (Allred, Harvey et al. 1998) have described one way of achieving this, which involved scoring both parameters on a scale from 0 (negative) to $3^+$, and summarizing the scores of the individual parameters to an overall score. This results in a scale with possible scores of 0, 2, 3, 4, 5, 6, 7 or 8. (Note that a score of 1 is not possible on Allred's scale). A somewhat simpler scoring method integrates the intensity of nuclear staining and the proportion of cells that display stained nuclei into a combined scale from 0 to $3^+$. Either scoring method may be applied to scoring intensity and proportion of staining of activated Stat5 in the cell nuclei. The terms positive or negative "cMet status" of tumors used in the present description refers to levels of expression of cMet that correspond to scores 0 or $1^+$-$3^+$ on the simplified scale, respectively.

Generally, the results of a test or assay according to the invention can be presented in any of a variety of formats. The results can be presented in a qualitative fashion. For example, the test report may indicate only whether or not a particular polypeptide was detected, perhaps also with an indication of the limits of detection. The results may be presented in a semi-quantitative fashion. For example, various ranges may be defined, and the ranges may be assigned a score (e.g., $1^+$ to $3^+$) that provides a certain degree of quantitative information. Such a score may reflect various factors, e.g., the number of cells in which cMet is detected, the intensity of the signal (which may indicate the level of expression of cMet or cMet bearing cells), etc. The results may be presented in a quantitative fashion, e.g., as a percentage of cells in which the polypeptide (cMet) is detected, as a protein concentration, etc. As will be appreciated by one of ordinary skill in the art, the type of output provided by a test will vary depending upon the technical limitations of the test and the biological significance associated with detection of the polypeptide. For example, in the case of certain polypeptides a purely qualitative output (e.g., whether or not the polypeptide is detected at a certain detection level) provides significant information. In other cases a more quantitative output (e.g., a ratio of the level of expression of the polypeptide in the sample being tested versus the normal level) is necessary.

In a more preferred embodiment, scoring of cMet expression level is graded from 0 to $3^+$, based on an assessment of the intensity of the reaction product and the percentage of positive cells. For more clarity, table 5 hereinafter summarizes these parameters. Only complete circumferential membranous reactivity of the invasive tumour should be considered and often resembled a "chicken wire" appearance. Under current guidelines, samples scored as borderline (score of $2^+$ or more) for cMet IHC must be considered as cMet(+) and are required to undergo further assessment. The IHC analysis should be rejected, and either repeated or confirmed by FISH or any other method if, as non limitative example, controls are not as expected, artifacts involve most of the sample and the sample has strong membranous positivity of normal breast ducts (internal controls) suggesting excessive antigen retrieval.

TABLE 5

| c-Met status | IHC description |
| --- | --- |
| 0 | No reactivity or membranous reactivity in less than 10% of tumour cells |
| $1^+$ | Faint/barely perceptible membranous reactivity is detected in more than 10% of tumour cells. The cells are immuno-reactive only in part of the membrane. |
| $2^+$ | Weak to moderate complete membranous reactivity is seen in more than 10% of tumour cells. |
| $3^+$ | Strong complete reactivity is seen in more than 10% of tumour cells. |

In a more preferred embodiment of the process according to the invention, said scoring comprises using an appropriate scale based on two parameters which are the intensity of the staining and the percentage of positive cells.

In a preferred embodiment, the process according to the invention, refers to an appropriate scale is a scale of 0 to $3^+$ wherein no membranous reactivity of tumor cells is scored 0, and strong complete reactivity in more than 10% of tumor cells is scored $3^+$.

In more details, as above described, said appropriate scale is a scale of 0 to 3 wherein no membranous reactivity of tumor cells is scored 0; faint perceptible membranous reactivity in more than 10% of tumor cells is scored $1^+$; weak to moderate complete membranous reactivity in more than 10% of tumor cells is scored $2^+$; and strong complete reactivity in more than 10% of tumor cells is scored $3^+$.

In a particular aspect of the invention, a tumor is cMet(+) with a score of $2^+$.

In a particular aspect of the invention, a tumor is cMet(+) with a score of $3^+$.

In another particular aspect of the invention, a tumor is cMet(+) with a score of $2^+$ or $3^+$.

According to the invention, it is also described a process of determining whether an oncogenic disorder is susceptible to treatment with a anti-cMet antibody, or a fragment or derivative thereof, wherein said process comprises the steps of (a) determining in vitro the cMet status of a tumor of a subject as above described, and (b) determining that, if the status is cMet(+), the oncogenic disorder is susceptible to treatment with an anti-cMet antibody, or a fragment or derivative thereof.

In another aspect of the invention, it is considered a kit useful for such diagnosing or prognosing process, said kit comprising the antibody of the invention.

As a matter of convenience, a packaged combination of reagents in predetermined amounts with instructions for performing the diagnostic assay, e.g. kits are also within the scope of the invention. The kit contains the antibodies for detection and quantitation of cMet in vitro, e.g. in an ELISA or a Western blot. The antibody of the present invention can be provided in a kit for detection and quantitation of cMet in vitro, e.g. in an ELISA or a Western blot. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. Such a kit may comprise a receptacle being compartmentalized to receive one or more containers such as vials, tubes and the like, such containers holding separate elements of the invention. For example, one container may contain a first antibody bound to an insoluble or partly soluble carrier. A second container may contain soluble, detectably-labeled second antibody, in lyophilized form or in solution. The receptacle may also contain a third container holding a detectably labeled third antibody in lyophilized form or in solution. A kit of this nature can be used in the sandwich assay of the invention. The label or package insert may provide a description of the composition as well as instructions for the intended in vitro or diagnostic use.

The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

In yet a further aspect of the invention, monoclonal antibodies or binding fragments thereof as detailed herein are provided labeled with a detectable moiety, such that they may be packaged and used, for example, in kits, to diagnose or identify cells having the aforementioned antigen. Non-limiting examples of such labels include fluorophores such as fluorescein isothiocyanate; chromophores, radionuclides, or enzymes. Such labeled antibodies or binding fragments may be used for the histological localization of the antigen, ELISA, cell sorting, as well as other immunological techniques for detecting or quantifying cMet, and cells bearing this antigen, for example.

Kits are also provided that are useful as a positive control for apoptosis assays, for purification or immunoprecipitation of cMet from cells. For isolation and purification of cMet, the kit can contain the antibodies described herein or antigen binding fragments thereof coupled to beads (e.g., sepharose beads). Kits can be provided which contain the antibodies for detection and quantitation of cMet in vitro, e.g. in an ELISA or a Western blot. As with the article of manufacture, the kit comprises a container and a label or package insert on or associated with the container. The container holds a composition comprising at least one anti-cMet antibody or binding fragment thereof of the invention. Additional containers may be included that contain, e.g., diluents and buffers, control antibodies. The label or package insert may provide a description of the composition as well as instructions for the intended in vitro or diagnostic use.

More particularly, the invention concerns a kit for the determination of the cMet status of a tumor by any method known by the man skilled in the art. In a preferred embodiment, as it will be described in the example, the invention relates to a kit for the determination of the cMet status of a tumor by IHC methods.

In a particular embodiment, the invention consists in a kit comprising at least an anti-c-Met antibody, or a functional fragment or derivative thereof, as above describes, said antibody being preferably labeled.

It must be understood that any labeling method can be used by the man skilled in the art such as, for example, the use of labels above mentioned.

In a preferred embodiment, the kit according to the invention, useful for detecting in vitro the presence and/or the location of a c-Met expressing tumor in a subject, further comprises a reagent useful for detecting the extent of binding between the said anti-c-Met antibody and c-Met.

In another preferred embodiment, the kit of the invention useful for determining in vitro the expression level of c-Met in a c-Met expressing tumor, further comprises a reagent useful for quantifying the level of binding between the said labeled antibody and c-Met.

In still another embodiment, the kit according to the invention useful for determining in vitro the c-Met status of a tumor, further comprises:

i) a reagent useful for detecting the extent of binding between the said labeled antibody and c-Met; and ii) positive and negative control samples useful for the scoring the c-Met expression level.

Said kit for determining in vitro the c-Met status of a tumor can further comprise a polyclonal antibody specific to murine antibodies, preferably said polyclonal antibody specific to murine antibodies is labeled.

Other characteristics and advantages of the invention appear in the continuation of the description with the examples and the figures whose legends are represented below.

Figure 1B:
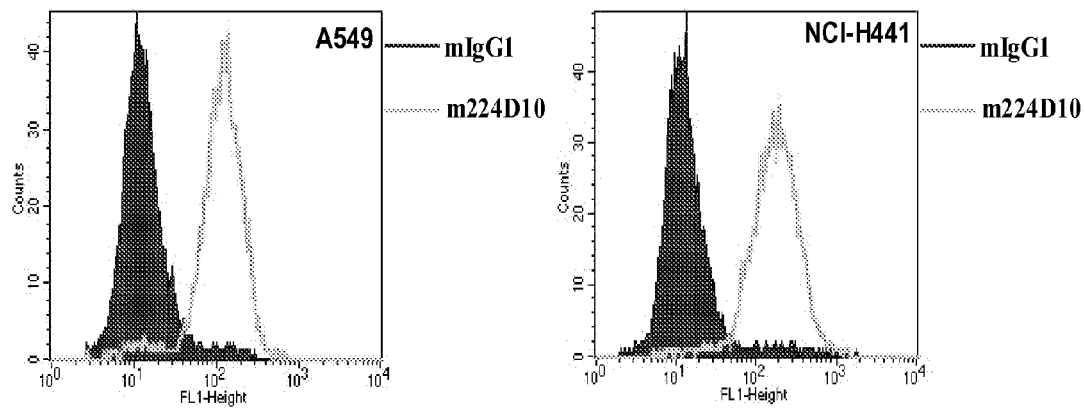

FIGS. 1A and 1B:
ELISA (FIG. A) and FACS (FIG. B) recognition of c-Met by the m224D10 Mab.

Figure 2:
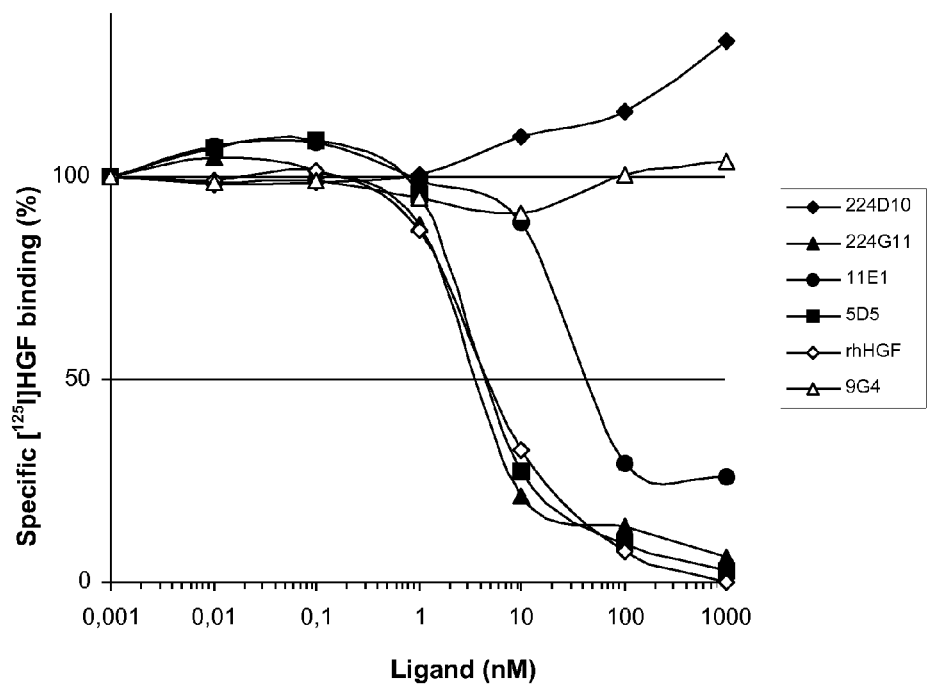

FIG. 2:
[125I]-HGF binding inhibition experiments. Total specific [$^{125}$I]-HGF binding (in %) was plotted as a function of ligand concentration on a semilog graph. Specific binding values are the means of experiments performed in triplicate.

Figures 3A, 3B:
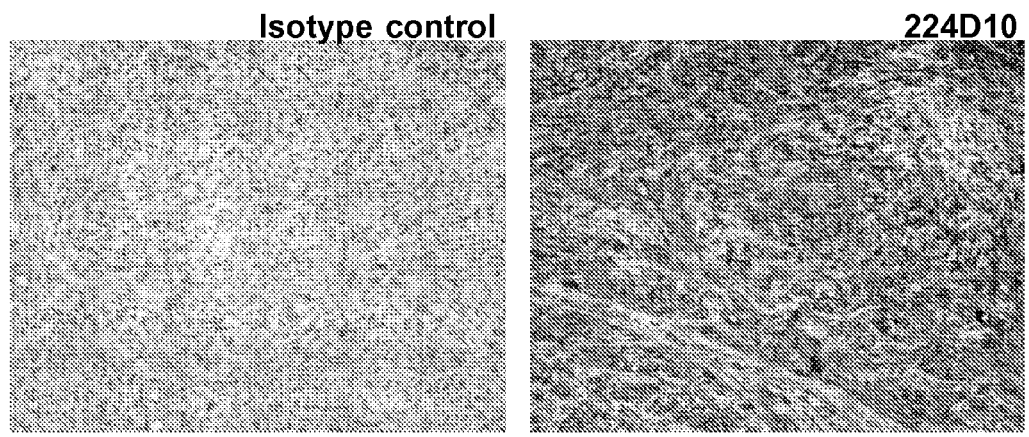

FIGS. 3A and 3B:
IHC analysis of paraffin-embedded sections from U87-MG xenografted tumors stained with an isotype control (FIG. 3A) and the m224D10 Mab (FIG. 3B).

Figure 4:
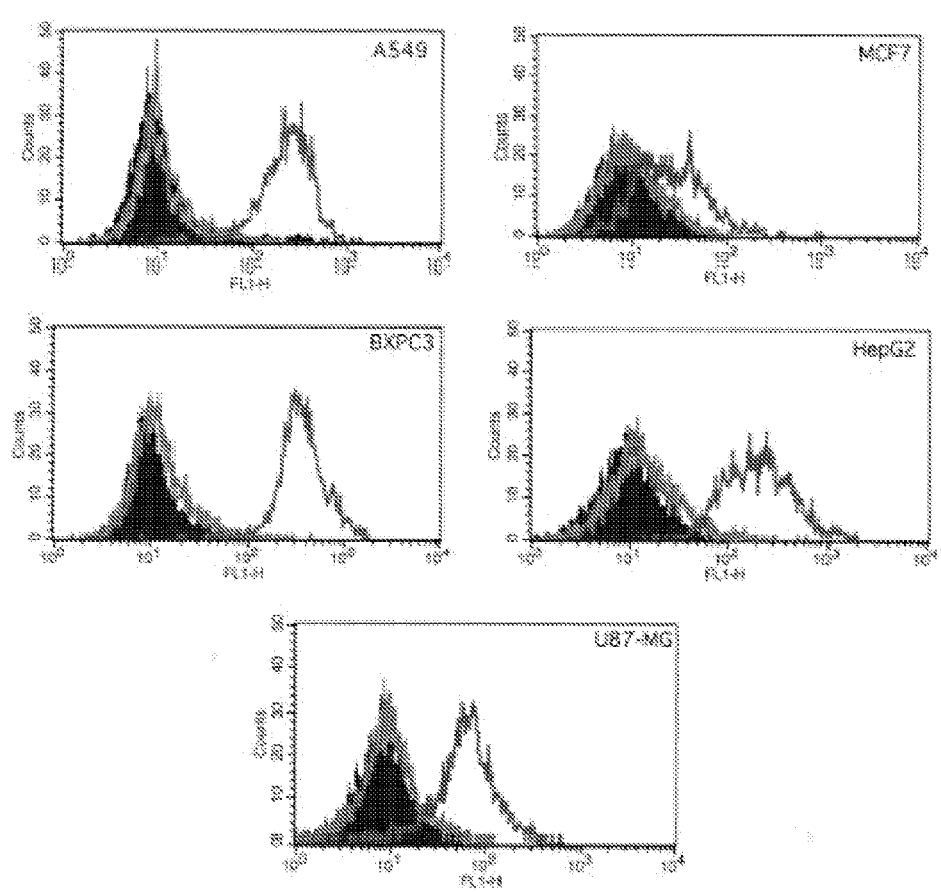

FIG. 4:
FACS recognition of c-Met by the m221C9 Mab

Figure 5A:
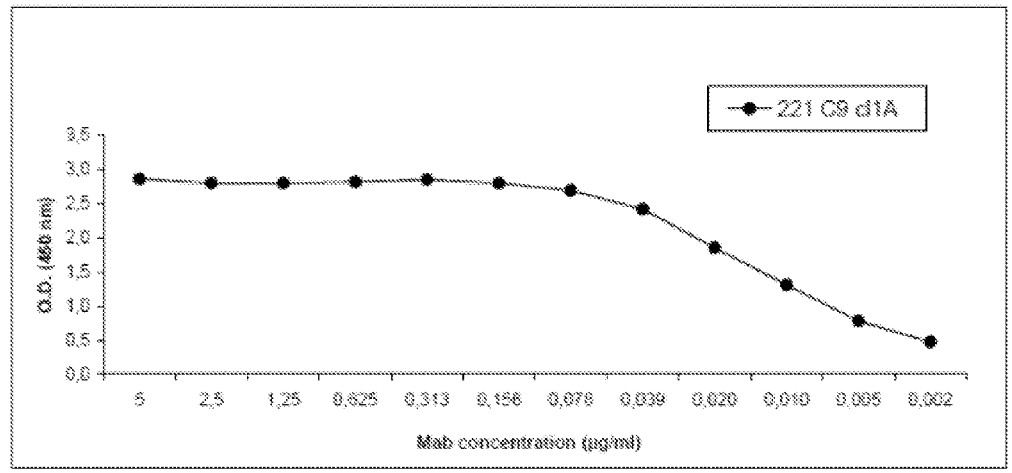
Figure 5B:
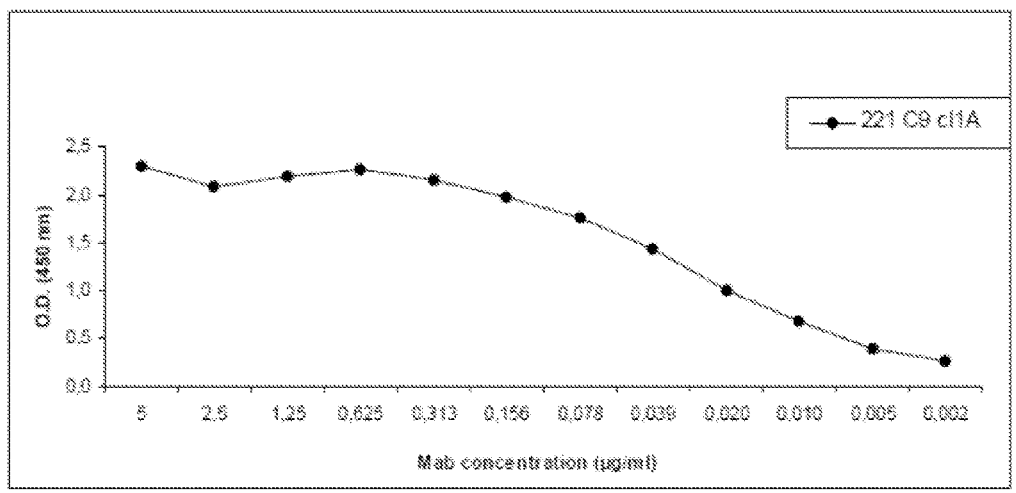

FIGS. 5A and 5B:
Titration curves of the 221C9 Mab on the immobilized dimeric (A) and monomeric (B) c-Met protein.

Figure 6:
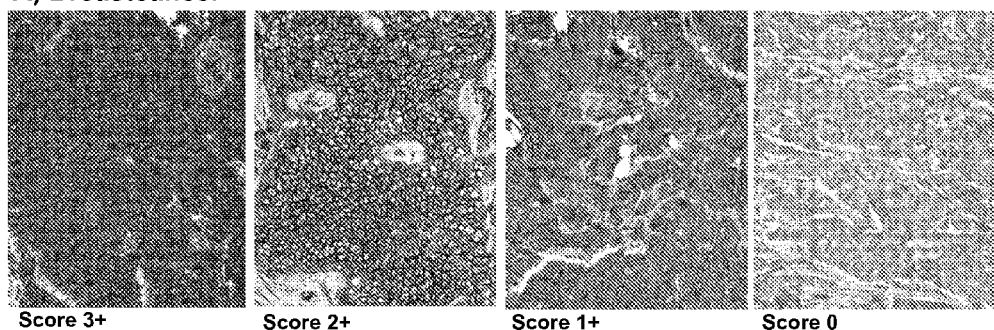
Figure 6:
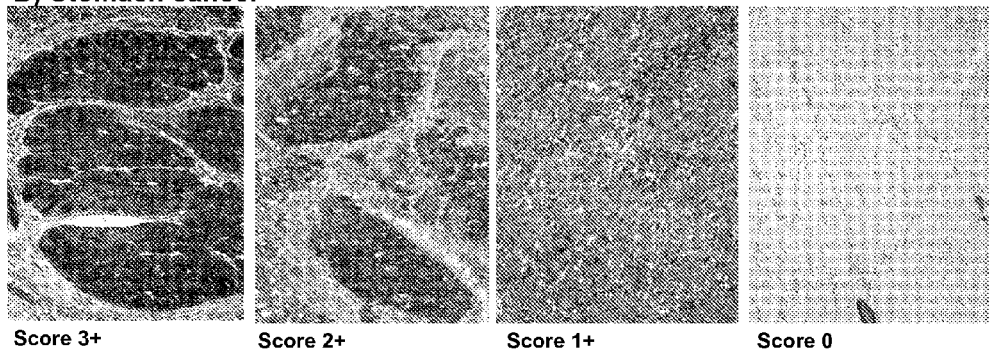

FIG. 6:
IHC staining of paraffin-embedded sections form breast (A) and stomach (B) tumor tissues expressing various levels of c-Met with m224D10.

Figure 7:
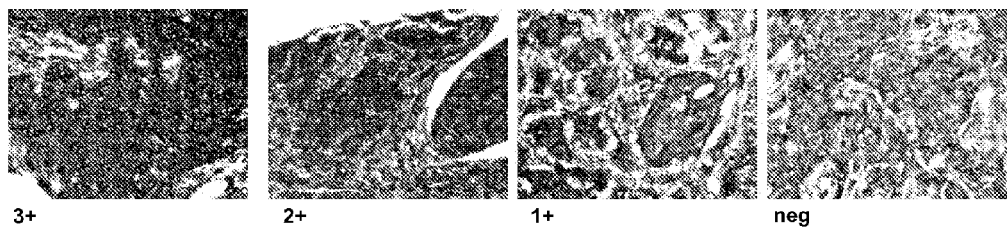
Figure 7:
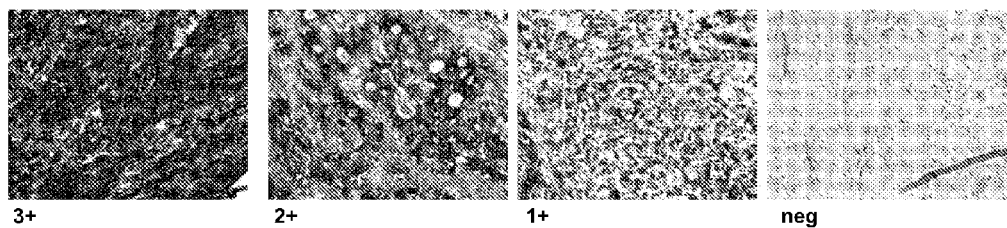

FIG. 7:
IHC staining of paraffin-embedded sections form breast (A) and stomach (B) tumor tissues expressing various levels of c-Met with m221C9.

Figure 8:
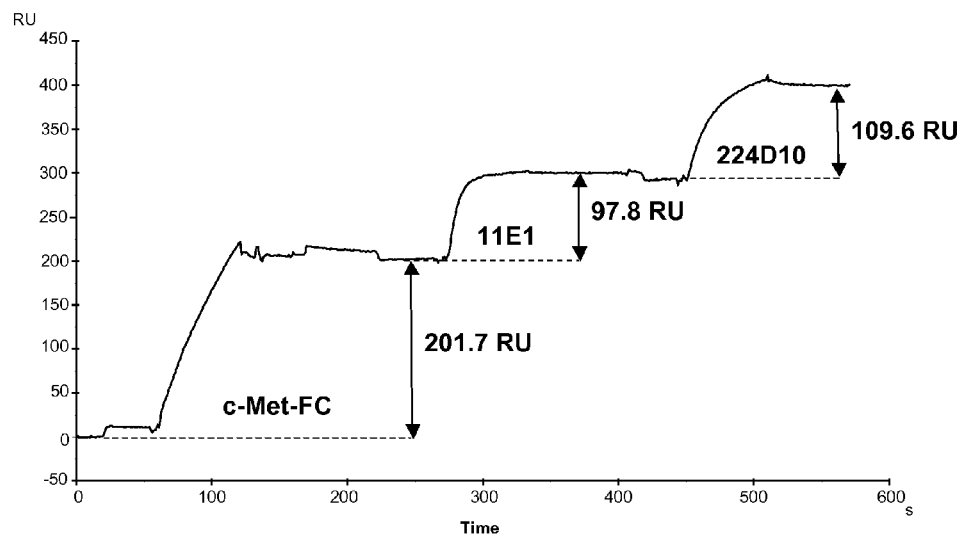

FIG. 8:
Sensorgram of the sequential injection of the Mabs 11E1 and 224D10 on 201.7 RU of captured c-Met-Fc on the flowcell 2 of a CM5 sensorchip activated by an anti-tag-His antibody.

Figure 9:
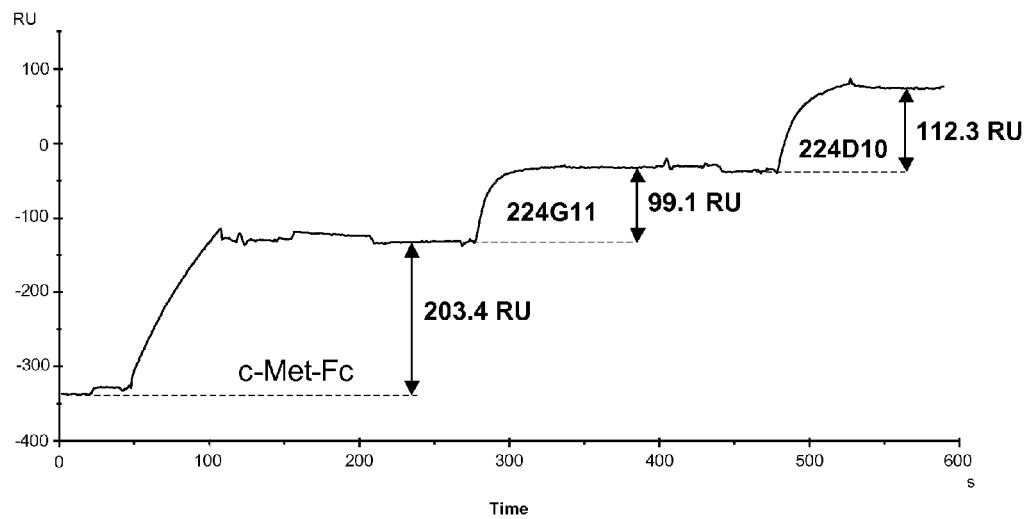

FIG. 9:
Sensorgram of the sequential injection of the Mabs 224G11 and 224D10 on 203.4 RU of captured c-Met-Fc on the flowcell 2 of a CM5 sensorchip activated by an anti-tag-His antibody.

Figure 10:
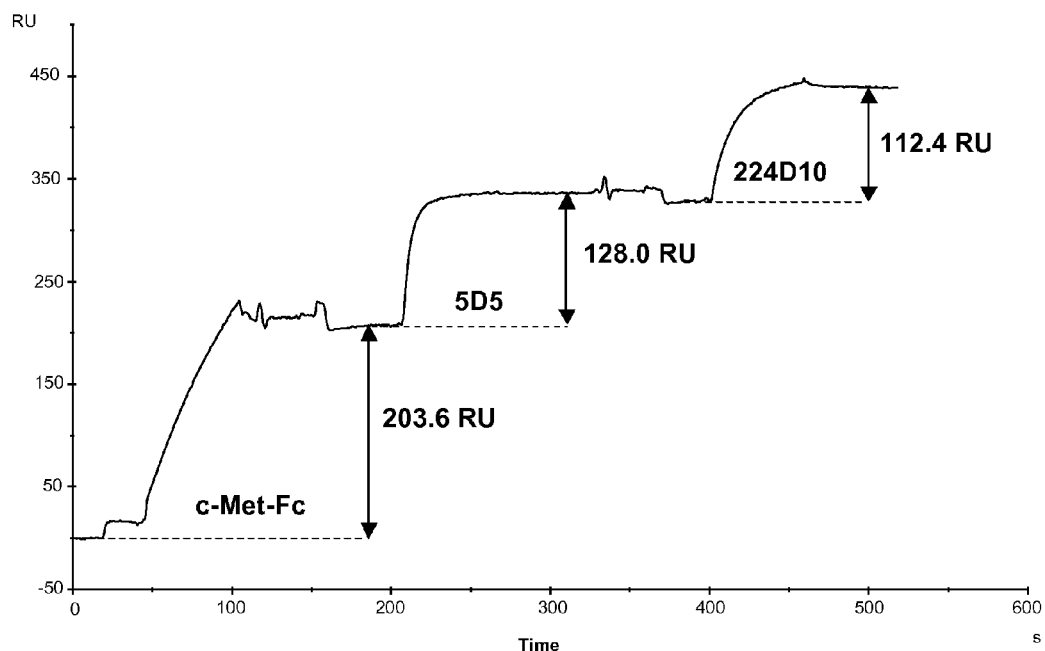

FIG. 10:
Sensorgram of the sequential injection of the Mabs 5D5 and 224D10 on 203.6 RU of captured c-Met-Fc on the flowcell 2 of a CM5 sensorchip activated by an anti-tag-His antibody.

Figure 11:
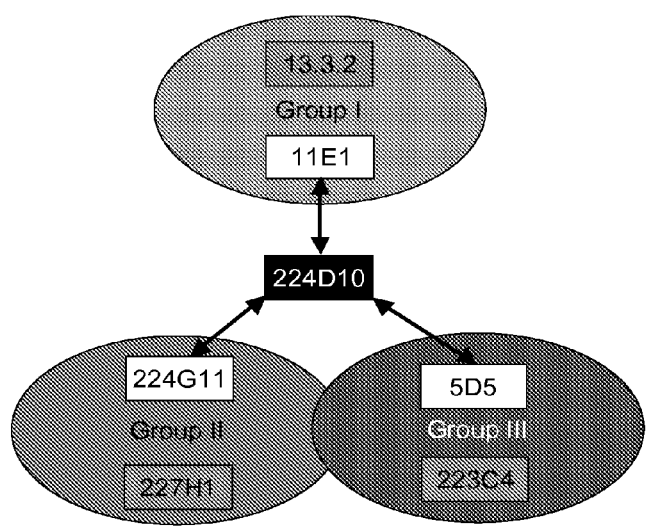

FIG. 11:
Epitope mapping scheme of the 7 anti-cMet antibodies. Arrows indicate the three experiments performed for this study. Grey squares indicate antibodies that have not been tested with 224D10.

Figure 12:
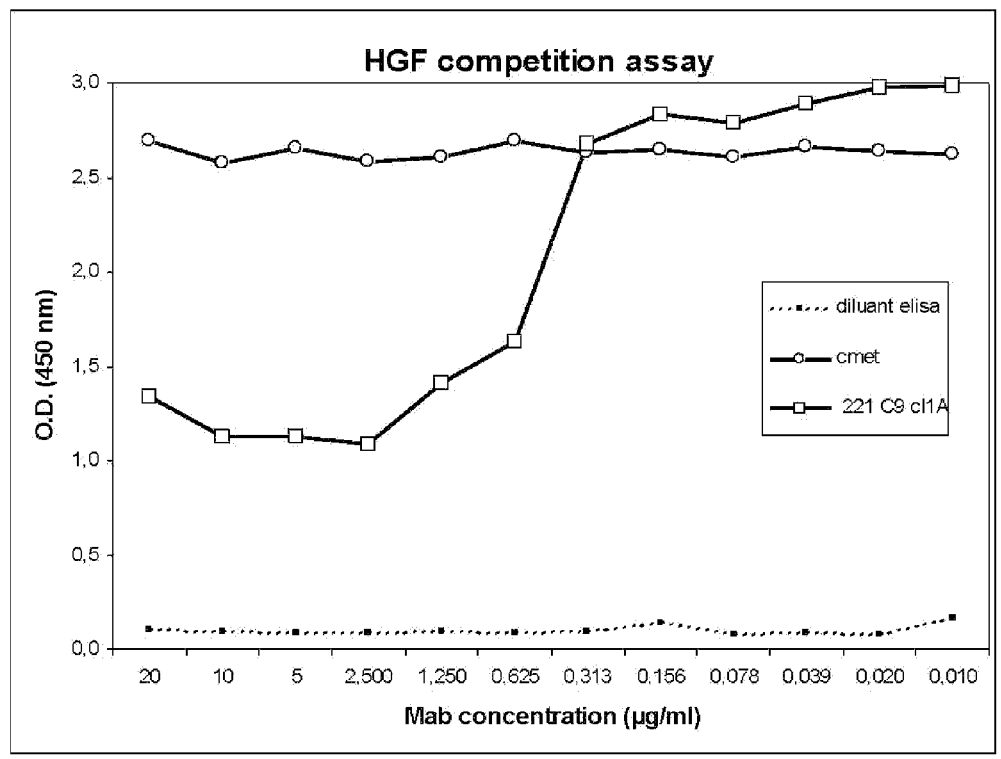

FIG. 12: HGF competition assay with m221C9 Mab.

EXAMPLE 1

Generation and Selection of Antibodies against cMet that Could be Used for Diagnostic Purpose Immunization Step To generate anti-cMet antibodies 8 weeks old BALB/c mice were immunized either 3 to 5 times subcutaneously with a CHO transfected cell line that express cMet on its plasma membrane ($20 \times 10^6$ cells/dose/mouse) or 2 to 3 times with a cMet extracellular domain fusion protein (10-15 µg/dose/mouse) (R&D Systems, Catalog #358MT) or fragments of this recombinant protein mixed with complete Freund adjuvant for the first immunization and incomplete Freund adjuvant for the following ones. Mixed protocols in which mice received both CHO-cMet cells and recombinant proteins were also performed. Three days before cell fusion, mice were boosted i.p. or i.v. with the recombinant protein or fragments. Then spleens of mice were collected and fused to SP2/0-Ag14 myeloma cells (ATCC) and subjected to HAT selection. In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation of hybridomas described by Kohler and Milstein (Nature, 256:495-497, 1975).

Screening Step for 224D10

Obtained hybridomas were initially screened by ELISA on the cMet recombinant protein. Briefly, the recombinant human c-Met-Fc protein (R&D systems) was coated overnight at 4° C. to Immulon II 96-well plates and, after a 1 h blocking step with a 0.5% gelatine solution, a dose range of m224G10 antibody was added for an additional 1 h at 37° C. Then plates were washed and a goat anti-mouse (Jackson) specific IgG HRP was added for 1 h at 37° C. Reaction development was performed using the TMB substrate solution. Then a second screen was performed by FACS analysis on A459 and NCI-H441 cell lines, that express moderate to high levels of c-Met, to be sure that the produced antibodies will be able to also recognize the native receptor on tumor cells. For that purpose $2 \times 10^5$ cells were incubated with a concentration range of either unconjugated 224D10 Mab or 9G4 (IgG1 isotype control Mab) for 20 min at 4° C. After 3 washings in phosphate-buffered saline (PBS) supplemented with 1% BSA and 0.01% $NaN_3$, cells were incubated with secondary antibody Goat anti-mouse Alexa 488 (dilution 1/500) for 20 minutes at 4° C. After 3 additional washings in PBS supplemented with 1% BSA and 0.1% $NaN_3$, cells were analyzed by FACS (Facscalibur, Becton-Dickinson). At least 5000 cells were assessed to calculate the mean value of fluorescence intensity.

Positive reactors on these 2 tests were amplified, cloned and a set of hybridomas was recovered, purified and screened for its lack of competition with radiolabelled HGF. Indeed a diagnostic antibody is usually needed both for patient selection and as a biomarker to follow the behaviour of the targeted receptor in patients treated with a therapeutic antibody. Regarding to this latter point, the major criteria to consider is that the diagnostic antibody must bind to an epitope different from the one recognized by the therapeutic antibody. One of the goal for a neutralizing therapeutic antibody directed against a growth factor receptor is to inhibit ligand binding. In that respect, during the selection of the diagnostic antibody, those that does not interfere with the ligand binding could be selected. In order to test that property, a competition assay of antibodies with radiolabelled HGF was set up. Briefly, protein A FlashPlate 96-well microplates (Perkin Elmer) were blocked with 0.5% gelatin in PBS (2 h at room temperature), before being coated overnight at 4° C. with the recombinant c-Met-Fc protein (R&D). Free residual Protein A sites were further saturated with a non relevant hIgG for 2 h at room temperature. Plates were washed with PBS after each step. For competition assays, binding of $[^{125}I]$-HGF (specific activity ~2,000 Ci/mmol) at 200 µM to immobilized c-Met was measured in the presence of varying concentrations of either the anti-c-Met monoclonal antibody to be tested or HGF (R&D Systems) ranging from 0.1 pM to 1 µM in PBS pH 7.4. Antibodies known for their capacity of displacing HGF (224G11, 11E1 and 5D5) were introduced as positive controls of the experiment. The 5D5 Mab is an antibody generated by Genentech and available as a hybridoma at the ATCC. A murine IgG1, described as 9G4, was used as an isotype control. The plates were then incubated at room temperature for 6 h and counted on a Packard Top Count Microplate Scintillation Counter. Non specific binding was determined in the presence of 1 µM of HGF.

Finally, Mabs that had fulfil the 3 criterias described above [i) c-Met recognition in an ELISA test, ii) binding on the native c-Met and iii) no competition with the radiolabelled ligand] were selected for the final c-Met recognition test on paraffin-embedded sections from tumor xenografts expressing c-Met. For that evaluation, tumor sections from U87-MG xenografts were deparaffinized, rehydrated, and placed in Target Retrieval Buffer 1× (Dako S1699) in a boiling bath pre-warm at 98° C. for heat-induced epitope retrieval at 98° C. for 30 minutes and then for 30 additional minutes in the Target Retrieval Buffer. After 3 washes in Tris Buffer Saline-0.05% tween 20 (TBS-T) (Dako S3006), the endogenous peroxidase activity was blocked using Peroxidase Blocking Reagent (Dako K4007) for five minutes. Sections were washed with TBS-T and incubated with blocking reagent (UltraV block-TA-125UB-LabVision) for 5 minutes before addition of the c-Met mouse monoclonal antibody to be tested (5 µg/ml). A mouse IgG1/kappa (5 µg/ml, X0931, Dako) was used as a negative control. Sections were then incubated overnight at 4° C., washed with TBS-T and incubated with biotinylated link universal (LSAB+, Dako K0679) for 15 minutes at room temperature. After washing with TBS-T, sections were incubated for 15 additional minutes with Streptavidin-peroxydase complex universal (LSAB+, Dako K0679). Diaminobenzidine was used for development of a brown reaction product.

Following a set of fusions, the murine 224D10 (m224D10) antibody was identified as a candidate for diagnostic of c-Met positive tumors. As exemplified in FIG. 1, the m224D10 is able to recognize c-Met both in an ELISA assay (FIG. 1A) and at the surface of A549 and NCI-H441 cell lines known to express c-Met (FIG. 1B).

The m224D10 was then tested in a radiolabelled HGF-displacement test. In FIG. 2, percent of total specific $[^{125}I]$-HGF binding was plotted as a function of ligand concentration on semilog graphs and concentrations of the various inhibitors required to inhibit the radioligand binding by 50% ($IC_{50}$) were determined graphically from the sigmoid competition curves obtained. As expected, non radio labeled HGF was able to fully displace $[^{125}I]$-HGF binding to immobilized c-Met, whereas the control antibody 9G4 did not show any HGF blocking activity. The anti-c-Met Mabs 224G11, 11E1 and 5D5, used as positive controls were able to inhibit $[^{125}I]$-HGF binding to immobilized c-Met, with $IC_{50}$ values of 3.6 nM, 42 nM and 4.4 nM, respectively. Mab m224D10 was unable to displace $[^{125}I]$-HGF and was selected for immunohistochemistry (IHC) studies.

Results shown in FIG. 3B demonstrated that m224G10 is able to recognize c-Met on U87-MG xenografted tumors known to be particularly sensitive to a c-Met targeted therapy. As expected no staining was observed with an IgG1 isotype control (FIG. 3A). Based on these results, experiments were set up to determine whether the 224D10 Mab could be used to score c-Met on tumors.

Screening Step for 221C9

Obtained hybridomas were initially screened by ELISA on the dimeric or monomeric cMet recombinant protein. Briefly, the recombinant human c-Met (dimeric or monomeric) proteins was coated overnight at 4° C. to Immulon II 96-well plates and, after a 1 h blocking step with a 0.5% gelatine solution, pure hybridoma supernatant was added for an additional 1 h at 37° C. Then plates were washed and a goat anti-mouse (Jackson) specific IgG HRP was added for 1 h at 37° C. Reaction development was performed using the TMB substrate solution. Then a second screen was performed by FACS analysis on A549 cell line, that express moderate to high levels of c-Met, to be sure that the produced antibodies will be able to also recognize the native receptor on tumor cells. For that purpose $2 \times 10^5$ cells were incubated with 10 µg/ml of m221C9 or m10D9 (IgG1 isotype control Mab) for 20 min at 4° C. After 3 washing in phosphate-buffered saline (PBS) supplemented with 1% BSA and 0.01% $NaN_3$, cells were incubated with secondary antibody Goat anti-mouse Alexa 488 (dilution 1/500) for 20 minutes at 4° C. After 3 additional washings in PBS supplemented with 1% BSA and 0.1% $NaN_3$, cells were analyzed by FACS (Facscalibur, Becton-Dickinson). At least 5000 cells were assessed to calculate the mean value of fluorescence intensity.

Positive hybridomas on these 2 tests were amplified, cloned, isotyped and expanded. Then new hybrid supernatants were collected. Their IgG content determined. Complementary cytometry analysis were performed on a panel of 5 human tumoral cell lines (A549, BXPC3, MCF7, U87MG, and HepG2). All these cell lines were provided by ATCC. Data obtained are presented in FIG. 4 and MFI values presented in Table 6 hereinafter.

TABLE 6

Data from cytometry analysis (MFI) performed with the 221C9 Mab on 5 tumoral human cell lines (ATCC)

|  | A549 | BXPC-3 | MCF7 | U87MG | HepG2 |
|---|---|---|---|---|---|
| Cells only | 13.98 | 11.87 | 9.87 | 9.10 | 10.52 |
| Secondary antibody | 11.98 | 13.23 | 11.10 | 11.20 | 15.85 |
| Isotype control | 11.83 | 14.77 | 12.06 | 11.56 | 18.12 |
| 221C9 | 243.59 | 375.57 | 31.95 | 71 | 233.58 |

Complementary experiments were done with purified 221C9 antibody. First antibody titration on both monomeric c-Met protein and dimeric c-Met protein was performed.

Titration curves are presented in FIG. 5. Similar affinity for either c-Met receptor forms was observed. To perform these ELISA the human dimeric c-Met protein (R&D sytems, cat #358MT) is coated at the concentration of 0.25 µg/ml in PBS overnight at 4° C. After saturation of the plates (Costar #3690) with a 0.5% gelatin solution 2 hours at 37° C., hybridoma supernatants are incubated 1 hour at 37° C. Once rinsed with PBS, the anti-mouse HRP-antibody (Jackson ImmunoResearch, catalog #115-035-164) is added to each well at a 1/5000 dilution in ELISA buffer (0.1% gelatin/0.05% Tween 20 in PBS) and the plates incubated for 1 hour at 37° C. After 3 washes in PBS, the activity of the peroxydase is revealed by the addition of 50 µl of TMB substrate (Uptima). The reaction is left to occur for 5 min at room temperature. The reaction is stopped by the addition of 50 µl/well of a 1 M $H_2SO_4$ solution and read on a plate reader at 450 nm. The same kind of protocol was performed on monomeric c-Met but in that case protein was coated at 5 µg/ml.

Finally, 221C9 Mab had fulfil the 2 criteria described above (i) c-Met recognition in an ELISA test, (ii) binding on the native c-Met expressed on the surface of human tumoral cell lines.

EXAMPLE 2

Scoring Tissues for c-Met Expression with the m224D10 and m221C9 Mabs

Using the protocol described above, a set of paraffin-embedded human tumor tissues, expressing variable levels of c-Met were stained with the m224D10 and m221C9 Mabs, respectively.

Results shown in FIG. 6 for the m224D10 and FIG. 7 for the m221C9 Mab demonstrated, in two tumor types, that both m224D10 and m221C9 are able to discriminate human tumors with variable levels of c-Met. Using these antibodies, tumors could be scored as:
  0 or neg: negative tumors in which no membrane staining or less than 10% membrane positive cell were observed,
  $1^+$: barely perceptible staining in more than 10% of tumor cells,
  $2^+$: Moderate complete membrane staining observed in more than 10% tumor cells,
  $3^+$: A strong complete staining of more than 10% of tumor cells.

EXAMPLE 3

224D10 Competition Experiments

As already written above a diagnostic Mab could also be used as a "response marker" for therapeutic antibodies that induce a down regulation of the targeted receptor. Regarding that point, blood or biopsies removal could be performed in treated patients and analyzed for c-Met status. For that purpose, the diagnostic antibody to be used must recognize an epitope different from the one targeted by the therapeutic antibody. As therapeutic antibodies are usually able to displace HGF, the selection of a diagnostic antibody that does not compete for ligand displacement could be helpful as a response marker for all therapeutic Mabs.

In this example competition experiments between 224D10 and many therapeutic Mabs was performed to demonstrate that 224D10 could be used as a response marker.

Therapeutic anti-c-Met Mabs 11E1, 227H1, 224G11 and the 5D5 Mab, which is the murin form of the one-armed 5D5, commercially available as a hybridoma at the ATCC, were studied in the biacore experiment. Briefly, a CM5 sensorchip is activated on flowcell 1 and 2 by covalently coupling the anti-polyhistidine Mab using the amine coupling kit following the supplier instructions. The running buffer is the HBS-EP buffer. The experiments are performed at 25° C. at a flow-rate of 30 µl/min. The HGF-R/Fc chimera protein is used at the concentration of 10 µg/ml in the running buffer and was injected for 1 minute over the flowcell 2. Typically, around 190 RU of c-Met-Fc were captured. The flowcell 1 served as a reference for the estimation of the non-specific binding of the Mabs. The first Mab (20 µg/ml) is injected for 2 minutes on both flowcell. The second antibody (20 µg/ml) was then injected on both flowcells. The differential Fc2-Fc1 resonance signal is recorded. At the end of each cycle, the sensorchip was regenerated by discarding the c-Met and Mabs proteins with an injection of the Glycine pH 1.5 regeneration buffer on both flowcells for half a minute.

The first experiment is carried out with 11E1 as the first antibody and 224D10 as the second antibody (see FIG. 8). This experiment shows that 11E1 and 224D10 bind to two distant epitope region at the surface of the c-Met-Fc molecule. The second experiment is carried out with 224G11 as the first antibody and 224D10 as the second antibody (see FIG. 9). This experiment shows that 224G11 and 224D10 bind to two distant regions too. The third experiment is carried out with 5D5 as the first antibody and 224D10 as the second antibody (see FIG. 10). Once again, this experiment shows that 5D5 and 224D10 bind to two distant regions. In conclusion 224D10 binds to a distant region on the c-Met molecule of the binding sites of 11E1, 224G11 and 5D5. Because, preliminary data obtained with the same kind of Biacore protocol, showed that the 13.3.2 anti c-Met antibody from Pfizer belongs to the same epitope mapping group as 11E1 (FIG. 11), we can suspect that 224D10 and 13.3.2 can bind simultaneously on the same c-Met molecule even if this combination have not be tested. Similarly for 227H1 which belongs to the same epitope group as 224G11 (FIG. 11), it is likely that both 227H1 and 224D10 antibodies could bind simultaneously to c-Met. Finally, 223C4 which belongs the same epitope mapping group as 5D5 (FIG. 11) could likely bind to c-Met simultaneously with 224D10.

EXAMPLE 4

HGF Competition Experiments Performed in Presence of the 221C9 Antibody

To further characterize the diagnostic Mabs, HGF competition assays were performed.

First reaction mixture comprising the c-Met protein in presence or not of the Mabs to be tested, are prepared on a separate saturated (0.5% gelatin in PBS 1×) plate. Serial 1:2 dilutions (starting from 40 µg/ml on 12 columns) of murine antibodies (references and Mabs to study) are performed. Then 0.8 µg/ml of the rh c-Met-Fc protein is added (RDSystems, ref. 358-MT/CF), except to the negative control line that contains only ELISA diluant (0.1% gelatin, 0.05% Tween 20 in PBS1×). After homogenisation, the competition samples are loaded on HGF-coated plates with a 0.3 µg/ml rhHGF solution in PBS (RDSystems, ref 294-HGN/CF). After an incubation and several washes, bound c-Met proteins are detected using a goat anti-Human IgG-HRP (Jackson, ref 109-035-098). Once bound, the TMB substrate is added to the plates. The reaction is stopped by addition of $H_2SO_4$ acid solution and the obtained optical densities read at 450 nm using a microplate reader instrument.

The experiment is carried out with 221C9 in presence or in absence of c-Met-Fc recombinant protein (see FIG. 12). This experiment shows that 221C9 is able to compete with the c-Met binding on its immobilized ligand receptor. However, in presence of 20 µg/ml of 221C9, only a partial binding of c-Met is observed.

The invention claimed is:

1. An isolated anti-cMET antibody, or a cMET-binding fragment thereof, wherein the antibody is selected from:
   a) an antibody comprising:
      a heavy chain comprising the following three CDRs as defined according to IMGT, respectively CDR-H1 having the sequence SEQ ID No. 7, CDR-H2 having the sequence SEQ ID No. 2 and CDR-H3 having the sequence SEQ ID No. 8, and
      a light chain comprising the following three CDRs as defined according to IMGT, respectively CDR-L1 having the sequence SEQ ID No. 4, CDR-L2 having the sequence SEQ ID No. 5 and CDR-L3 having the sequence SEQ ID No. 6; and
   b) an antibody comprising:
      a heavy chain comprising the following three CDRs as defined according to IMGT, respectively CDR-H1 having the sequence SEQ ID No. 29, CDR-H2 having the sequence SEQ ID No. 30 and CDR-H3 having the sequence SEQ ID No. 31; and
      a light chain comprising the following three CDRs as defined according to IMGT, respectively CDR-L1 having the sequence SEQ ID No. 32, CDR-L2 having the sequence SEQ ID No. 33 and CDR-L3 having the sequence SEQ ID No. 34.

2. An isolated antibody, or a cMET-binding fragment thereof, according to claim 1, wherein the antibody from comprises:
   a) a heavy chain variable domain having the amino acid sequence SEQ ID No. 13 and a light chain variable domain having the amino acid sequence SEQ ID No. 14; or
   b) a heavy chain variable domain having the amino acid sequence SEQ ID No. 40 and a light chain variable domain having the amino acid sequence SEQ ID No. 41.

3. An isolated antibody, or a cMET-binding fragment thereof, according to claim 1, wherein the antibody is a murine antibody.

4. An isolated antibody, or a cMET-binding fragment thereof, according to claim 1, wherein the antibody does not block the binding of the ligand HGF to the cMET protein.

5. A murine hybridoma capable of secreting an antibody according to claim 1, said murine hybridoma being selected from the hybridoma deposited at the CNCM, Institut Pasteur, Paris, France on Mar. 12, 2008 under the number I-3949 and the hybridoma deposited at the CNCM, Institut Pasteur, Paris, France on Jan. 14, 2010 under the number I-4273.

6. An isolated nucleic acid coding for the light chain and/or the heavy chain variable domains of an antibody as claimed in claim 2.

7. A method for diagnosing an oncogenic disorder associated with expression of cMET in a sample, or for determining the prognosis for developing an oncogenic disorder associated with expression of cMET in a sample, comprising contacting an antibody according to claim 1, or a cMET-binding fragment thereof, to said sample to detect cMET expression in the sample.

8. A process of detecting the presence and/or the location of a cMET expressing tumor in a subject, wherein said process comprises (a) contacting a sample from the subject with an anti-cMET antibody, or a cMET-binding fragment thereof, according to claim 1, and (b) detecting the binding of said antibody, or of said cMET-binding fragment, to the sample.

9. A process of determining the expression level of cMET in a cMET-expressing tumor from a subject, wherein said process comprises (a') contacting a sample from the subject with an anti-cMET antibody, or a cMET-binding fragment thereof, according to claim 1, and (b') quantifying the level of binding of said antibody, or of said cMET-binding fragment, to cMET in said sample.

10. A process according to claim 9, wherein the cMET expression level is measured by immunohistochemistry (IHC).

11. A process of diagnosing a cMET-expressing tumor or determining the prognosis for developing a cMET-expressing tumor in a subject, wherein said process comprises (i) determining the expression level of cMET according to claim 9, and (ii) comparing the expression level of step (i) with a reference expression level of cMET from normal tissue.

12. A process of determining the cMET status of a tumor from a subject, wherein said process comprises (1) determining the expression level of cMET according to claim 9, (2) scoring said tumor for cMET expression level, and (3) comparing said scoring to that obtained from a control sample.

13. A process according to claim 12, wherein said scoring comprises using an appropriate scale based on two parameters which are the intensity of the staining and the percentage of positive cells.

14. A process according to claim 13, wherein said appropriate scale is a scale of 0 to $3^+$ wherein no membranous reactivity of tumor cells is scored 0, and strong complete reactivity in more than 10% of tumor cells is scored $3^+$.

15. A process according to claim 14, wherein said appropriate scale is a scale of 0 to 3 wherein no membranous reactivity of tumor cells is scored 0; faint perceptible membranous reactivity in more than 10% of tumor cells is scored $1^+$; weak to moderate complete membranous reactivity in more than 10% of tumor cells is scored $2^+$; and strong complete reactivity in more than 10% of tumor cells is scored $3^+$.

16. A process according to claim 14, wherein a tumor is cMET (+) with a score of $2^+$ or $3^+$.

17. A process of determining whether an oncogenic disorder is susceptible to treatment with an anti-cMET antibody, or binding fragment thereof, wherein said process comprises (a) determining the cMET status of a tumor of a subject according to claim 16, and (b) determining if the status is cMET (+), the oncogenic disorder is susceptible to treatment with the anti-cMET antibody, or binding fragment thereof.

18. A kit comprising at least one anti-cMET antibody, or binding fragment thereof, according to claim 1, said antibody optionally being labeled.

19. A kit according to claim 18 for detecting the presence and/or the location of a cMET expressing tumor in a subject, said kit comprising a reagent useful for detecting the extent of binding between the anti-cMET antibody, or binding fragment thereof, and cMET.

20. A kit according to claim 18 for determining the expression level of cMET in a cMET-expressing tumor, said kit comprising a reagent useful for quantifying the level of binding between the anti-cMET antibody, or binding fragment thereof, and cMET.

21. A kit according to claim 18 for determining the cMET status of a tumor, said kit further comprising:
   i) a reagent useful for detecting the extent of binding between the anti-cMET antibody, or binding fragment thereof, and cMET; and
   ii) positive and negative control samples useful for the scoring the cMET expression level.

22. A kit according to claim 21 for determining the cMET status of a tumor, said kit further comprising a polyclonal antibody specific to murine antibodies.

23. A kit according to claim 22 wherein, said polyclonal antibody specific to murine antibodies is labeled.

\* \* \* \* \*

UNITED STATES PATENT AND TRADEMARK OFFICE
CERTIFICATE OF CORRECTION

PATENT NO.        : 8,673,302 B2                                     Page 1 of 1
APPLICATION NO.   : 13/391435
DATED             : March 18, 2014
INVENTOR(S)       : Goetsch et al.

It is certified that error appears in the above-identified patent and that said Letters Patent is hereby corrected as shown below:

In the Claims

Claim 2, Col. 57, Line 59, "antibody from" should read as --antibody--.

Signed and Sealed this
Seventeenth Day of June, 2014

Michelle K. Lee
*Deputy Director of the United States Patent and Trademark Office*

SEQUENCE LISTING

```
<160> NUMBER OF SEQ ID NOS: 60

<210> SEQ ID NO 1
<211> LENGTH: 5
<212> TYPE: PRT
<213> ORGANISM: mus musculus

<400> SEQUENCE: 1

Thr Ser Ala Tyr Phe
1               5

<210> SEQ ID NO 2
<211> LENGTH: 7
<212> TYPE: PRT
<213> ORGANISM: mus musculus

<400> SEQUENCE: 2

Ile Asn Tyr Asp Gly Thr Asn
1               5

<210> SEQ ID NO 3
<211> LENGTH: 6
<212> TYPE: PRT
<213> ORGANISM: mus musculus

<400> SEQUENCE: 3

Asp Arg Thr Phe Ala Tyr
1               5

<210> SEQ ID NO 4
<211> LENGTH: 6
<212> TYPE: PRT
<213> ORGANISM: mus musculus

<400> SEQUENCE: 4

Gln Arg Ile Tyr Asn Tyr
1               5
```

```
<210> SEQ ID NO 5
<211> LENGTH: 3
<212> TYPE: PRT
<213> ORGANISM: mus musculus

<400> SEQUENCE: 5

Tyr Ala Ser
1

<210> SEQ ID NO 6
<211> LENGTH: 9
<212> TYPE: PRT
<213> ORGANISM: mus musculus

<400> SEQUENCE: 6

Gln Gln Ser Asn Ser Trp Pro Leu Thr
1               5

<210> SEQ ID NO 7
<211> LENGTH: 9
<212> TYPE: PRT
<213> ORGANISM: mus musculus

<400> SEQUENCE: 7

Gly Tyr Ser Ile Thr Ser Ala Tyr Phe
1               5

<210> SEQ ID NO 8
<211> LENGTH: 8
<212> TYPE: PRT
<213> ORGANISM: mus musculus

<400> SEQUENCE: 8

Thr Arg Asp Arg Thr Phe Ala Tyr
1               5

<210> SEQ ID NO 9
<211> LENGTH: 7
<212> TYPE: PRT
<213> ORGANISM: mus musculus

<400> SEQUENCE: 9

Thr Ser Ala Tyr Phe Trp Ser
1               5

<210> SEQ ID NO 10
<211> LENGTH: 16
<212> TYPE: PRT
<213> ORGANISM: mus musculus

<400> SEQUENCE: 10

Phe Ile Asn Tyr Asp Gly Thr Asn Asn Tyr Asn Pro Ser Leu Lys Asn
1               5                   10                  15

<210> SEQ ID NO 11
<211> LENGTH: 11
<212> TYPE: PRT
<213> ORGANISM: mus musculus

<400> SEQUENCE: 11

Arg Ala Ser Gln Arg Ile Tyr Asn Tyr Leu His
1               5                   10
```

<210> SEQ ID NO 12
<211> LENGTH: 7
<212> TYPE: PRT
<213> ORGANISM: mus musculus

<400> SEQUENCE: 12

Tyr Ala Ser Gln Ser Ile Ser
1               5

<210> SEQ ID NO 13
<211> LENGTH: 115
<212> TYPE: PRT
<213> ORGANISM: mus musculus

<400> SEQUENCE: 13

Asp Leu Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Ala
            20                  25                  30

Tyr Phe Trp Ser Trp Ile Arg Gln Phe Pro Gly Asn Lys Leu Glu Trp
        35                  40                  45

Met Gly Phe Ile Asn Tyr Asp Gly Thr Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Arg Leu Asn Ser Val Thr Thr Asp Asp Thr Ala Thr Tyr Tyr Cys
                85                  90                  95

Thr Arg Asp Arg Thr Phe Ala Tyr Trp Gly Gln Gly Thr Leu Val Thr
            100                 105                 110

Val Ser Ala
        115

<210> SEQ ID NO 14
<211> LENGTH: 107
<212> TYPE: PRT
<213> ORGANISM: mus musculus

<400> SEQUENCE: 14

Asp Ile Val Leu Thr Gln Ser Pro Ala Thr Leu Ser Val Thr Pro Gly
1               5                   10                  15

Asp Arg Val Ser Leu Ser Cys Arg Ala Ser Gln Arg Ile Tyr Asn Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Ile Leu Thr Ile Asn Ser Val Glu Thr
65                  70                  75                  80

Glu Asp Phe Gly Met Tyr Phe Cys Gln Gln Ser Asn Ser Trp Pro Leu
                85                  90                  95

Thr Phe Gly Ala Gly Thr Lys Leu Glu Leu Arg
            100                 105

<210> SEQ ID NO 15
<211> LENGTH: 15
<212> TYPE: DNA
<213> ORGANISM: mus musculus

<400> SEQUENCE: 15
accagtgctt atttc                                                    15

-continued

```
<210> SEQ ID NO 16
<211> LENGTH: 21
<212> TYPE: DNA
<213> ORGANISM: mus musculus

<400> SEQUENCE: 16
ataaactacg acggtaccaa t                                              21

<210> SEQ ID NO 17
<211> LENGTH: 18
<212> TYPE: DNA
<213> ORGANISM: mus musculus

<400> SEQUENCE: 17
gatcggacct ttgcttat                                                  18

<210> SEQ ID NO 18
<211> LENGTH: 18
<212> TYPE: DNA
<213> ORGANISM: mus musculus

<400> SEQUENCE: 18
caaagaattt acaactac                                                  18

<210> SEQ ID NO 19
<211> LENGTH: 9
<212> TYPE: DNA
<213> ORGANISM: mus musculus

<400> SEQUENCE: 19 tatgcttcc                                                             9

<210> SEQ ID NO 20
<211> LENGTH: 27
<212> TYPE: DNA
<213> ORGANISM: mus musculus

<400> SEQUENCE: 20
caacagagta acagctggcc tctcacg                                        27

<210> SEQ ID NO 21
<211> LENGTH: 27
<212> TYPE: DNA
<213> ORGANISM: mus musculus

<400> SEQUENCE: 21
ggctactcca tcaccagtgc ttatttc                                        27

<210> SEQ ID NO 22
<211> LENGTH: 24
<212> TYPE: DNA
<213> ORGANISM: mus musculus

<400> SEQUENCE: 22
acaagagatc ggacctttgc ttat                                           24

<210> SEQ ID NO 23
<211> LENGTH: 21
<212> TYPE: DNA
<213> ORGANISM: mus musculus

<400> SEQUENCE: 23
accagtgctt atttctggag c                                              21
```

<210> SEQ ID NO 24
<211> LENGTH: 48
<212> TYPE: DNA
<213> ORGANISM: mus musculus

<400> SEQUENCE: 24
ttcataaact acgacggtac caataactac aacccatctc tcaaaaat                     48

<210> SEQ ID NO 25
<211> LENGTH: 33
<212> TYPE: DNA
<213> ORGANISM: mus musculus

<400> SEQUENCE: 25
agggccagtc aaagaattta caactaccta cac                                    33

<210> SEQ ID NO 26
<211> LENGTH: 21
<212> TYPE: DNA
<213> ORGANISM: mus musculus

<400> SEQUENCE: 26
tatgcttccc agtccatctc t                                                 21

<210> SEQ ID NO 27
<211> LENGTH: 345
<212> TYPE: DNA
<213> ORGANISM: mus musculus

<400> SEQUENCE: 27
gatctacagc ttcaggagtc aggacctggc ctcgtgaaac cttctcagtc tctgtctctc        60
acctgctctg tcactggcta ctccatcacc agtgcttatt tctggagctg gatccggcag       120
tttccaggaa acaaactgga atggatgggc ttcataaact acgacggtac caataactac       180
aacccatctc tcaaaaatcg aatctccatc actcgtgata catctaagaa ccagttttc        240 ctgaggttga attctgtgac tactgacgac acagctacgt attactgtac aagagatcgg       300
acctttgctt attggggcca agggactctg gtcactgtct ctgca                      345

<210> SEQ ID NO 28
<211> LENGTH: 321
<212> TYPE: DNA
<213> ORGANISM: mus musculus

<400> SEQUENCE: 28
gatattgtgt taactcagtc tccagccacc ctgtctgtga ctccaggaga tagagtcagt        60
ctttcctgca gggccagtca aagaatttac aactacctac actggtatca acaaaaatca       120
catgagtctc caaggcttct catcaagtat gcttcccagt ccatctctgg gatcccctcc       180
aggttcagtg gcagtggctc agggacagat ttcattctca ctatcaacag tgtggagact       240
gaagattttg gaatgtattt ctgtcaacag agtaacagct ggcctctcac gttcggtgct       300
gggaccaagc tggagctgag a                                                 321

<210> SEQ ID NO 29
<211> LENGTH: 8
<212> TYPE: PRT
<213> ORGANISM: Mus musculus

<400> SEQUENCE: 29

Gly Tyr Thr Phe Thr Ser Tyr Trp
1               5

```
<210> SEQ ID NO 30
<211> LENGTH: 8
<212> TYPE: PRT
<213> ORGANISM: Mus musculus

<400> SEQUENCE: 30

Ile Asn Pro Ser Asn Gly Arg Thr
1               5

<210> SEQ ID NO 31
<211> LENGTH: 10
<212> TYPE: PRT
<213> ORGANISM: Mus musculus

<400> SEQUENCE: 31

Ala Arg Arg Val Gly Tyr Leu Met Asp Tyr
1               5                   10

<210> SEQ ID NO 32
<211> LENGTH: 5
<212> TYPE: PRT
<213> ORGANISM: Mus musculus

<400> SEQUENCE: 32

Ser Ser Val Ser Tyr
1               5

<210> SEQ ID NO 33
<211> LENGTH: 3
<212> TYPE: PRT
<213> ORGANISM: Mus musculus

<400> SEQUENCE: 33

Asp Thr Ser
1

<210> SEQ ID NO 34
<211> LENGTH: 9
<212> TYPE: PRT
<213> ORGANISM: Mus musculus

<400> SEQUENCE: 34

Gln Gln Trp Asn Ser Asn Pro Pro Thr
1               5

<210> SEQ ID NO 35
<211> LENGTH: 5
<212> TYPE: PRT
<213> ORGANISM: Mus musculus

<400> SEQUENCE: 35

Ser Tyr Trp Met His
1               5

<210> SEQ ID NO 36
<211> LENGTH: 17
<212> TYPE: PRT
<213> ORGANISM: Mus musculus

<400> SEQUENCE: 36

Glu Ile Asn Pro Ser Asn Gly Arg Thr His Tyr Asn Glu Lys Phe Arg
1               5                   10                  15

Thr
```

```
<210> SEQ ID NO 37
<211> LENGTH: 8
<212> TYPE: PRT
<213> ORGANISM: Mus musculus

<400> SEQUENCE: 37

Arg Val Gly Tyr Leu Met Asp Tyr
1               5

<210> SEQ ID NO 38
<211> LENGTH: 10
<212> TYPE: PRT
<213> ORGANISM: Mus musculus

<400> SEQUENCE: 38

Ser Ala Ser Ser Val Ser Tyr Met His
1               5                   10

<210> SEQ ID NO 39
<211> LENGTH: 7
<212> TYPE: PRT
<213> ORGANISM: Mus musculus

<400> SEQUENCE: 39

Asp Thr Ser Lys Leu Ala Ser
1               5

<210> SEQ ID NO 40
<211> LENGTH: 117
<212> TYPE: PRT
<213> ORGANISM: Mus musculus

<400> SEQUENCE: 40

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr His Tyr Asn Glu Lys Phe
    50                  55                  60

Arg Thr Lys Ala Thr Leu Thr Val Ala Lys Ser Ser Ile Thr Ala Tyr
65                  70                  75                  80

Met Gln Leu Ser Thr Leu Thr Ser Glu Asp Ser Ala Val Tyr Tyr Cys
                85                  90                  95

Ala Arg Arg Val Gly Tyr Leu Met Asp Tyr Trp Gly Gln Gly Thr Ser
            100                 105                 110

Val Thr Ala Pro Gln
        115

<210> SEQ ID NO 41
<211> LENGTH: 106
<212> TYPE: PRT
<213> ORGANISM: Mus musculus

<400> SEQUENCE: 41

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Leu Ile Tyr
        35                  40                  45
```

```
Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Ser Asn Pro Pro Thr
                85                  90                  95

Phe Gly Ala Gly Thr Lys Leu Glu Leu Lys
            100                 105

<210> SEQ ID NO 42
<211> LENGTH: 24
<212> TYPE: DNA
<213> ORGANISM: Mus musculus

<400> SEQUENCE: 42
ggctacacct tcaccagcta ctgg                                    24

<210> SEQ ID NO 43
<211> LENGTH: 24
<212> TYPE: DNA
<213> ORGANISM: Mus musculus

<400> SEQUENCE: 43
attaatccta gcaacggtcg tact                                    24

<210> SEQ ID NO 44
<211> LENGTH: 30
<212> TYPE: DNA
<213> ORGANISM: Mus musculus

<400> SEQUENCE: 44
gcaagaaggg ttggttacct catggactac                              30

<210> SEQ ID NO 45
<211> LENGTH: 15
<212> TYPE: DNA
<213> ORGANISM: Mus musculus

<400> SEQUENCE: 45
tcaagtgtaa gttac                                              15

<210> SEQ ID NO 46
<211> LENGTH: 9
<212> TYPE: DNA
<213> ORGANISM: Mus musculus

<400> SEQUENCE: 46 gacacatcc                                                      9

<210> SEQ ID NO 47
<211> LENGTH: 27
<212> TYPE: DNA
<213> ORGANISM: Mus musculus

<400> SEQUENCE: 47
cagcagtgga atagtaaccc acccacg                                 27

<210> SEQ ID NO 48
<211> LENGTH: 15
<212> TYPE: DNA
<213> ORGANISM: Mus musculus
```

```
<400> SEQUENCE: 48
agctactgga tgcac                                                     15

<210> SEQ ID NO 49
<211> LENGTH: 51
<212> TYPE: DNA
<213> ORGANISM: Mus musculus

<400> SEQUENCE: 49
gagattaatc ctagcaacgg tcgtactcac tacaatgaga agttcaggac c              51

<210> SEQ ID NO 50
<211> LENGTH: 24
<212> TYPE: DNA
<213> ORGANISM: Mus musculus

<400> SEQUENCE: 50
agggttggtt acctcatgga ctac                                           24

<210> SEQ ID NO 51
<211> LENGTH: 30
<212> TYPE: DNA
<213> ORGANISM: Mus musculus

<400> SEQUENCE: 51
agtgccagct caagtgtaag ttacatgcac                                     30

<210> SEQ ID NO 52
<211> LENGTH: 21
<212> TYPE: DNA
<213> ORGANISM: Mus musculus

<400> SEQUENCE: 52
gacacatcca aactggcttc t                                              21

<210> SEQ ID NO 53
<211> LENGTH: 351
<212> TYPE: DNA
<213> ORGANISM: Mus musculus

<400> SEQUENCE: 53
caggtccaac tgcagcagcc tggggctgaa ctggtgaagc ctggggcttc agtgaagctg      60
tcctgcaagg cttctggcta caccttcacc agctactgga tgcactgggt gaagcagagg     120
cctggacaag gccttgagtg gattggagag attaatccta gcaacggtcg tactcactac     180
aatgagaagt tcaggaccaa ggccacactg actgttgcca atcctccat cacagcctac      240 atgcaactca gcaccctgac atctgaggac tctgcggtct attactgtgc aagaagggtt     300
ggttacctca tggactactg gggtcaagga acctcagtca ccgctcctca g              351

<210> SEQ ID NO 54
<211> LENGTH: 318
<212> TYPE: DNA
<213> ORGANISM: Mus musculus

<400> SEQUENCE: 54
caaattgttc tcacccagtc tccagcaatc atgtctgcat ctccagggga gaaggtcacc      60
atgacctgca gtgccagctc aagtgtaagt tacatgcact ggtaccagca gaagtcaggc     120
acctccccca aaagattgat ttatgacaca tccaaactgg cttctggagt ccctgctcgc     180
ttcagtggca gtgggtctgg gacctcttac tctctcacaa tcagcagcat ggaggctgaa     240
```

```
gatgctgcca cttattactg ccagcagtgg aatagtaacc cacccacgtt cggtgctggg    300
accaagctgg agctgaaa                                                  318
```

```
<210> SEQ ID NO 55
<211> LENGTH: 9
<212> TYPE: PRT
<213> ORGANISM: artificial
<220> FEATURE:
<223> OTHER INFORMATION: Sequence from CDR-H1
<220> FEATURE:
<221> NAME/KEY: misc_feature
<222> LOCATION: (3)..(3)
<223> OTHER INFORMATION: Xaa is S or T
<220> FEATURE:
<221> NAME/KEY: misc_feature
<222> LOCATION: (4)..(4)
<223> OTHER INFORMATION: Xaa is I or F
<220> FEATURE:
<221> NAME/KEY: misc_feature
<222> LOCATION: (7)..(7)
<223> OTHER INFORMATION: Xaa is A or missing
<220> FEATURE:
<221> NAME/KEY: misc_feature
<222> LOCATION: (9)..(9)
<223> OTHER INFORMATION: Xaa is F or W

<400> SEQUENCE: 55

Gly Tyr Xaa Xaa Thr Ser Xaa Tyr Xaa
1               5

<210> SEQ ID NO 56
<211> LENGTH: 8
<212> TYPE: PRT
<213> ORGANISM: artificial
<220> FEATURE:
<223> OTHER INFORMATION: Sequence from CDR-H2
<220> FEATURE:
<221> NAME/KEY: misc_feature
<222> LOCATION: (3)..(3)
<223> OTHER INFORMATION: Xaa is Y or P
<220> FEATURE:
<221> NAME/KEY: misc_feature
<222> LOCATION: (4)..(4)
<223> OTHER INFORMATION: Xaa is D or S
<220> FEATURE:
<221> NAME/KEY: misc_feature
<222> LOCATION: (5)..(5)
<223> OTHER INFORMATION: Xaa is N or missing
<220> FEATURE:
<221> NAME/KEY: misc_feature
<222> LOCATION: (7)..(7)
<223> OTHER INFORMATION: Xaa is T or R
<220> FEATURE:
<221> NAME/KEY: misc_feature
<222> LOCATION: (8)..(8)
<223> OTHER INFORMATION: Xaa is N or T

<400> SEQUENCE: 56

Ile Asn Xaa Xaa Xaa Gly Xaa Xaa
1               5

<210> SEQ ID NO 57
<211> LENGTH: 10
<212> TYPE: PRT
<213> ORGANISM: artificial
<220> FEATURE:
<223> OTHER INFORMATION: Sequence from CDR-H3
<220> FEATURE:
<221> NAME/KEY: misc_feature
<222> LOCATION: (1)..(1)
<223> OTHER INFORMATION: Xaa is T or A
```

```
<220> FEATURE:
<221> NAME/KEY: misc_feature
<222> LOCATION: (3)..(3)
<223> OTHER INFORMATION: Xaa is D or R
<220> FEATURE:
<221> NAME/KEY: misc_feature
<222> LOCATION: (4)..(4)
<223> OTHER INFORMATION: Xaa is R or V
<220> FEATURE:
<221> NAME/KEY: misc_feature
<222> LOCATION: (5)..(5)
<223> OTHER INFORMATION: Xaa is T or G
<220> FEATURE:
<221> NAME/KEY: misc_feature
<222> LOCATION: (6)..(6)
<223> OTHER INFORMATION: Xaa is F or Y
<220> FEATURE:
<221> NAME/KEY: misc_feature
<222> LOCATION: (7)..(7)
<223> OTHER INFORMATION: Xaa is A or L
<220> FEATURE:
<221> NAME/KEY: misc_feature
<222> LOCATION: (8)..(8)
<223> OTHER INFORMATION: Xaa is M or missing
<220> FEATURE:
<221> NAME/KEY: misc_feature
<222> LOCATION: (9)..(9)
<223> OTHER INFORMATION: Xaa is D or missing

<400> SEQUENCE: 57

Xaa Arg Xaa Xaa Xaa Xaa Xaa Xaa Xaa Tyr
1               5                   10

<210> SEQ ID NO 58
<211> LENGTH: 6
<212> TYPE: PRT
<213> ORGANISM: artificial
<220> FEATURE:
<223> OTHER INFORMATION: Sequence from CDR-L1
<220> FEATURE:
<221> NAME/KEY: misc_feature
<222> LOCATION: (1)..(1)
<223> OTHER INFORMATION: Xaa is Q or missing
<220> FEATURE:
<221> NAME/KEY: misc_feature
<222> LOCATION: (2)..(2)
<223> OTHER INFORMATION: Xaa is R or S
<220> FEATURE:
<221> NAME/KEY: misc_feature
<222> LOCATION: (3)..(3)
<223> OTHER INFORMATION: Xaa is I or S
<220> FEATURE:
<221> NAME/KEY: misc_feature
<222> LOCATION: (4)..(4)
<223> OTHER INFORMATION: Xaa is Y or V
<220> FEATURE:
<221> NAME/KEY: misc_feature
<222> LOCATION: (5)..(5)
<223> OTHER INFORMATION: Xaa is N or S

<400> SEQUENCE: 58

Xaa Xaa Xaa Xaa Xaa Tyr
1               5

<210> SEQ ID NO 59
<211> LENGTH: 3
<212> TYPE: PRT
<213> ORGANISM: artificial
<220> FEATURE:
<223> OTHER INFORMATION: Sequence from CDR-L2
<220> FEATURE:
<221> NAME/KEY: misc_feature
<222> LOCATION: (1)..(1)
<223> OTHER INFORMATION: Xaa is Y or D
```

```
<220> FEATURE:
<221> NAME/KEY: misc_feature
<222> LOCATION: (2)..(2)
<223> OTHER INFORMATION: Xaa is A or T

<400> SEQUENCE: 59

Xaa Xaa Ser
1

<210> SEQ ID NO 60
<211> LENGTH: 9
<212> TYPE: PRT
<213> ORGANISM: artificial
<220> FEATURE:
<223> OTHER INFORMATION: Sequence from CDR-L3
<220> FEATURE:
<221> NAME/KEY: misc_feature
<222> LOCATION: (3)..(3)
<223> OTHER INFORMATION: Xaa is S or W
<220> FEATURE:
<221> NAME/KEY: misc_feature
<222> LOCATION: (6)..(6)
<223> OTHER INFORMATION: Xaa is W or N
<220> FEATURE:
<221> NAME/KEY: misc_feature
<222> LOCATION: (8)..(8)
<223> OTHER INFORMATION: Xaa is L or P

<400> SEQUENCE: 60

Gln Gln Xaa Asn Ser Xaa Pro Xaa Thr
1               5
```